US008838211B2

(12) United States Patent
Melendez et al.

(10) Patent No.: US 8,838,211 B2
(45) Date of Patent: Sep. 16, 2014

(54) MULTI-WAVELENGTH DIAGNOSTIC IMAGER

(75) Inventors: Jose Melendez, Lakeway, TX (US); James Watson, Plano, TX (US); John Michael DiMaio, Dallas, TX (US); Roma Moza, Plano, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 612 days.

(21) Appl. No.: 12/433,639

(22) Filed: Apr. 30, 2009

(65) Prior Publication Data
US 2009/0275841 A1 Nov. 5, 2009

Related U.S. Application Data

(60) Provisional application No. 61/049,243, filed on Apr. 30, 2008, provisional application No. 61/146,223, filed on Jan. 21, 2009.

(51) Int. Cl.
*A61B 5/00* (2006.01)
*A61G 7/10* (2006.01)
*A61B 6/04* (2006.01)
*G01N 21/88* (2006.01)
*A61B 6/00* (2006.01)
*A61G 7/015* (2006.01)

(52) U.S. Cl.
CPC .............. *A61G 7/1025* (2013.01); *A61B 5/447* (2013.01); *A61B 5/00* (2013.01); *A61B 6/04* (2013.01); *G01N 21/8851* (2013.01); *A61B 5/0059* (2013.01); *A61B 5/6887* (2013.01); *A61B 2576/00* (2013.01); *A61B 6/56* (2013.01); *A61G 7/015* (2013.01); *A61G 2210/20* (2013.01)
USPC ........................................... 600/476; 600/300

(58) Field of Classification Search
USPC ......... 600/407, 425, 427, 430, 473, 476, 300; 5/600, 601, 940; 340/573.1; 382/128
See application file for complete search history.

(56) References Cited

U.S. PATENT DOCUMENTS 6,205,354 B1 3/2001 Gellermann et al.
6,287,253 B1 9/2001 Ortega et al.
(Continued)

FOREIGN PATENT DOCUMENTS

KR 10-0690205 B1 3/2007
WO 0078217 A1 12/2000
(Continued)

OTHER PUBLICATIONS

Leachtenauer et al. "A Non-Contact Imaging-Based Approach to Detecting Stage I Pressure Ulcers", Engineering in Medicine and Biology Society, 2006. EMBS '06. 28th Annual International Conference of the IEEE, vol., No. pp. 6380-6383, Aug. 30, 2006-Sep. 3, 2006. doi: 10.1109/IEMBS.2006.259513.*

(Continued)

*Primary Examiner* — Unsu Jung
*Assistant Examiner* — Phong K Huynh
(74) *Attorney, Agent, or Firm* — Edwin S. Flores; Chalker Flores, LLP

(57) ABSTRACT

The present invention is a multi-wavelength diagnostic imager. In one embodiment, the present invention includes an apparatus and method for noninvasive evaluation of a target versus a non-target, comprising: one or more light sources having at least one emission spectra directed at the target wherein the position, orientation and intensity of light sources is varied to control near-surface reflectance and are directed at less than the entire target; and one or more detectors positioned to capture light reflected from the target into two or more spatial images of the target at two or more times, wherein the spatial images are used to distinguish between the target and the non-target.

54 Claims, 28 Drawing Sheets

(56) References Cited

U.S. PATENT DOCUMENTS

| | | | |
|---|---|---|---|
| 6,351,573 B1* | 2/2002 | Schneider | 382/128 |
| 7,155,273 B2 | 12/2006 | Taylor | |
| 2002/0016533 A1* | 2/2002 | Marchitto et al. | 600/310 |
| 2003/0159219 A1 | 8/2003 | Harrison et al. | |
| 2005/0124864 A1* | 6/2005 | Mack et al. | 600/300 |
| 2006/0152378 A1 | 7/2006 | Lokhorst et al. | |
| 2006/0278240 A1 | 12/2006 | Spillman, Jr. et al. | |
| 2007/0073156 A1 | 3/2007 | Zilberman et al. | |
| 2008/0060138 A1 | 3/2008 | Price et al. | |
| 2009/0163819 A1 | 6/2009 | De Kok et al. | |

FOREIGN PATENT DOCUMENTS

| | | | |
|---|---|---|---|
| WO | 2007020643 A2 | 2/2007 | |
| WO | 2007144810 A1 | 12/2007 | |

OTHER PUBLICATIONS

Sonenblum et al. "Non-Invasive Erythema Detection Using Spectral Imaging." Proceeding of RESNA 2005 Annual Conference, Atlanta, Georgia, 2005.*

Bennett et al. "Paraplegic pressure sore frequency versus circulation measurements". Journal of Rehabilitation Research and Development vol. 27 No. 2, 1990 pp. 115-126.*

International Search Report and Written Opinion for PCT/US2009/042436 dated Dec. 23, 2009.

International Search Report and Written Opinion for PCT/US2009/042440 dated Jun. 28, 2010.

Allen, John, "Photoplethysmography and its Application in Clinical Physiological Measurement," Physiol. Meas., (2007), 28:R1-R39.

Bello, Ysabel M., et al., "Recent Advances in Wound Healing," JAMA, Feb. 9, 2000, vol. 283, No. 6, pp. 716-718.

Binzoni, T., et al., "Detection Limits of Multi-Spectral Optical Imaging Under the Skin Surface," Phys. Med. Biol., (2008), 53:617-636.

Humphreys, K., et al., "A CMOS Camera-Based Pulse Oximetry Imaging System," Proceedings of the 2005 IEEE Engineering in Medicine and Biology 27th Annual Conference, Shanghai, China, Sep. 1-4, 2005, pp. 3494-3497.

Humphreys, Kenneth, et al., "Noncontact Simultaneoud Dual Wavelength Photoplethysmography: A Further Step Toward Noncontact Pulse Oximetry," Review of Scienfitic Instruments, (2007), 78:044304-1-044304-6.

Kerekes, John, et al., "Spectral Imaging of Skin: Experimental Observations and Analyses," Proceedings of SPIE vol., (2006), 6142, pp. 61423V-1-61423V-,8.

Leonardi, Lorenzo, et al., "Evaluating the Health of Compromised Tissues Using a Near Infrared Spectroscopic Imaging System in Clinical Settings: Lessons Learned," Proceedings of SPIE, (2003), vol. 4959, pp. 89-99.

Mansfield, James R., et al., "Tissue Viability by Multispectral Near Infrared Imaging: A Fuzzy C-Means Clustering Analysis," IEEE Transactions on Medical Imaging, Dec. 1998, vol. 17, No. 6, pp. 1011-1018.

Palero, J.A., et al., "In Vivo Nonlinerar Spectral Imaging in Mouse Skin," Optics Express, May 15, 2006, vol. 14, No. 10, 8 pages.

Payette, Jeri R., et al., "Assessment of Skin Flaps Unsing Optically Based Methods for Measuring Blood Flow and Oxygenation," Plast. Reconstr. Surg., (2005), 115:539-546.

Shannon, Claude E., "Communication in the Presence of Noise," Proceedings of the IRE, Jan. 1949, vol. 37, No. 1, pp. 10-21.

Stamatas, Georgios N., et al., "In Vivo Monitoring of Cutaneous Edema Using Spectral Imaging in the Visible and Near Infrared," Journal of Investigative Dermatology, (2006), 126, pp. 1753-1760.

Texas Instruments, "TMS320DM6437 Digital Media Processor Data Sheet," Nov. 2006, 305 pages.

Wieringa, FP., et al., In Vitro Demonstration of an Sp02-Camera, Computers in Cardiology, (2007), 34:749-751.

Hauben, Daniel Joseph, et al., "On the History of the Free Skin Graft," Annals of Plastic Surgery, Sep. 1982, vol. 9, No. 3, pp. 242-246.

Jones, Robert H., et al., "Coronary Bypass Surgery with or without Surgical Ventri1717.cular Reconstruction," The New England Journal of Medicine, Apr. 23, 2009, vol. 360, No. 17, pp. 1705-1717.

Wieringa, F. P., et al., "Contactless Multiple Wavelength Photoplethysmographic Imaging: A First Step Toward "SpO2 Camera" Technology," Annals of Biomedical Engineering, Aug. 2005, vol. 33, No. 8, pp. 1034-1041.

* cited by examiner

MULTI-WAVELENGTH DIAGNOSTIC IMAGER

CROSS-REFERENCE TO RELATED APPLICATIONS

This application claims priority to U.S. Provisional Application Ser. No. 61/146,223, filed Jan. 21, 2009 and U.S. Provisional Application Ser. No. 61/049,243, filed Apr. 30, 2008.

TECHNICAL FIELD OF THE INVENTION

The present invention relates in general to the field of noninvasive medical imaging, and more particularly, to the design and application of multi-wavelength imaging to distinguishing between a target and a non-target based on the differing frequency behaviors of the spatial images, for example, patient care.

STATEMENT OF FEDERALLY FUNDED RESEARCH

None.

BACKGROUND OF THE INVENTION

Without limiting the scope of the invention, its background is described in connection with devices that aid in patient diagnosis, care and treatment.

Modern day decubitus ulcer prevention involves inexact nursing protocols and a variety of questionable products lacking clinically verifiable patient outcomes. This situation is today's reality despite the fact that several hundred thousand cases of decubitus ulcers are reported each year in the United States alone, comprising an estimated $13 billion dollars of associated healthcare costs. Currently, no sufficient standardized care protocol has been accepted for ulcer prevention, and nurses are largely left with the physical burden of moving the patient every two hours while visually observing the skin for signs of obvious breakdown.

Specialized bed surfaces (i.e., mattresses) are often used that rest on a frame and provide direct patient support over relatively small ranges of motion. Their primary function is to alleviate the pressure commonly found in a patient's head, back, buttocks, and heel areas. To reduce ulcer risk, patient positioning may be performed via a set of hinges, slides, and motorized articulations; enabling poses such as flat, Trendelenburg (normal and reverse), vascular (raised legs), dining/sitting, and upright transitioning. Beyond the various positions defined, bed surfaces are commercially available in a wide range of cost and sophistication (major categories including passive foam/gel mattress; passive multi-chamber fluid/pneumatic systems; open-loop active pneumatics; and closed-loop active pneumatics) that may utilize pressure, displacement and strain sensing technologies to adjust individual chamber pressure. However, the problem with every existing approach lies in the lack of any physiological data from the patient that directly relates to tissue degradation. While the presence of pressure is necessary for bed sore formation, it is not a sufficient condition. As such, redistribution of pressure points is not always necessary or proven to be always effective. By the time that visual degeneration is noticed, substantial tissue death below the skin surface has already occurred. This delayed detection results in decubitus ulcers that, once treated, may take two years to return to original tissue health. As a high-cost and high-volume problem in hospitals today, care protocols must move away from efficient treatment towards automated and effective prevention of decubitus ulcers.

SUMMARY OF THE INVENTION

The present invention is an imaging apparatus and method for multi-wavelength detection and imaging. The present invention includes an apparatus and method for noninvasive evaluation of a target versus a non-target, comprising: one or more light sources having at least one emission spectra directed at the target wherein the position, orientation and intensity of light sources is varied to control near-surface reflectance and are directed at less than the entire target; and one or more detectors positioned to capture light reflected from the target into two or more spatial images of the target at two or more times, wherein the spatial images are used to distinguish between the target and the non-target. In one aspect, the apparatus further comprising a processor in communication with the one or more detectors, wherein the processor further calculates a transform of the time variations of at least a portion of the spatial images to distinguish between target and non-target image information to measure the presence of one or more factors that lead to changes in tissue health selected from decubitus ulcers, cancerous lesions, skin transfers, skin temperature, skin oxygenation, burns, skin trauma, skin diseases, autoinflammatory diseases, autoimmune diseases, infectious diseases, and combinations thereof. In one aspect, the position, orientation and intensity of light sources is selected to reduce or eliminate specular and near-surface reflectance.

In one embodiment the present invention describes an apparatus for noninvasive evaluation of a target versus a non-target, comprising: (i) two or more light sources directed at the target each of the light sources having a defined emission spectra and angle of illumination; (ii) one or more detectors positioned to capture light from the target into two or more spatial images of the target into spatial images of the target at two or more times, wherein the spatial images are used to distinguish between the target and the non-target based on, e.g., differing frequency behaviors. In one aspect, the apparatus further comprises a processor in communication with the one or more detectors, wherein the processor further calculates a transform of the time variations of at least a portion of the spatial images to distinguish between target and non-target image information to measure the presence of one or more factors that lead to decubitus ulcers.

Another embodiment of the present invention is an apparatus for noninvasive measurement of a target versus a non-target, comprising: (i) two or more light sources each of the light sources having a defined emission spectra and angle of illumination; (ii) one or more detectors positioned to capture light from a target comprising one or more two dimensional spatial images of the target; and (iii) a processor in communication with the light sources and detectors, wherein the processor calculates a transform of the time variations of at least a portion of the spatial images to distinguish between target and non-target image information based on differing frequency behaviors.

In one aspect of the apparatus of the present invention the transform of the time variations of at least a portion of the spatial image information is a discrete Fourier transform. In another aspect, the processor of the apparatus of the present invention further calculates a transform of at least a portion of the spatial image information to further distinguish between target and non-target image information based on differing inverse spatial behaviors. In yet another aspect the position, orientation and intensity of light sources in the apparatus of the present invention is selected to reduce or eliminate specular reflectance.

The apparatus of the present invention further comprises, (i) one or more distance standards positioned at a known distance from the detector, (ii) one or more intensity reference standards positioned to diffusely reflect light from the light sources into the detector to calibrate the detector, (iii) one or more object references positioned to diffusely reflect light from the light sources into the detector to calibrate the detector. The two or more light sources in the apparatus comprise light emitting diodes under control of the processor, wherein the processor can individually trigger each of the light emitting diodes or combinations thereof. In the apparatus of the present invention the detector is nearly parallel to the target surface.

In one aspect the processor in the apparatus of the present invention further detects the interface between target and non-target portions of an image captured by the detector. In a further aspect the apparatus of the present invention comprises a base module positioned in a pressurizable chamber to illuminate the target surface, wherein the pressure within the chamber is controlled by the processor. In another aspect the input/output module of the present imaging apparatus further comprises a wireless connection in the base in the form of a two-way wireless communication system for transferring data between the processor and a data collection/processing system.

In another aspect, the imaging process of the apparatus of the present invention can determine when a property of the target or non-target is close to a determined level and the processor can trigger an alarm if the processor detects one or more of the following parameters: a change in surface conditions, movement, moisture, temperature changes, a solid object, a liquid, a vital sign, oxygenation changes, pressure, pulse rate, and respiration rate. The processor of the present imaging apparatus can detect by taking any of continuous and semi-continuous measurements and use time based information and trends to perform various functions, comprising any of: estimation of precision, estimation of confidence intervals, and prediction of future events.

In yet another aspect the apparatus of the present invention further comprises one or more sources of background light, a patient support capable of moving the target in two or three dimensions, wherein the support comprises a pressurized chamber. The patient support and apparatus of the present invention are capable of capturing an entire patient image in one or more target images. In a further aspect of the present invention, the two or more light sources and detectors comprise part of an array of detector modules capable of concurrently capturing an entire patient image, and the one or more light sources and the one or more detectors are embedded within a mattress.

In yet another embodiment the present invention describes an apparatus for noninvasive measurement of a target versus a non-target, comprising: (i) two or more light sources each of the light sources having a defined emission spectra and angle of illumination; (ii) one or more detectors positioned to capture a target reflection comprising one or more two dimensional spatial images of the target; and (iii) a processor in communication with the light sources and the detectors, wherein the processor calculates a transform of at least a portion of the one or more spatial images to distinguish between a target portion and a non-target portion in the two dimensional spatial images based on differing inverse spatial behaviors between the target and the non-target.

In one aspect, the processor in the present imaging apparatus further calculates a transform of one or more time variations of the at least a portion of the spatial images to further distinguish between target and non-target based on differing frequency behaviors, wherein the transform of the at least a portion of the spatial image information is a discrete Fourier transform. In another aspect, the apparatus is handheld. In another aspect, the processor is programmed with a predetermined set of positions for a target support, wherein deformations of the target support cause one or more specular reflections that saturate the detector, wherein the processor turns off one or more light sources within an array of light sources that cause specular reflections of the target support.

In a further embodiment the present invention is an imaging apparatus for detecting conditions of a portion of a living body target versus a non-target leading to decubitus ulcers, comprising: (i) two or more light sources each of the light sources having a defined emission spectra and angle of illumination for targeting a portion of the living body; (ii) one or more detectors positioned to capture a reflection from the living body comprising one or more two dimensional spatial images of the target; and (iii) a processor in communication with the light sources and detectors, wherein the processor calculates a transform of the time variations of the at least a portion of the spatial images to distinguish between target and non-target image information based on differing frequency behaviors to determine the presence of one or more factors that lead to decubitus ulcers.

In one aspect the apparatus of the present invention further comprises one or more sources of background light, a patient support comprising a pressurized chamber capable of moving the target in two or three dimensions. In a further aspect the patient support and the apparatus are capable of capturing an entire patient image in one or more target images. In another aspect of the present invention the two or more light sources and the one or more detectors comprise a detector module in the form of an array capable of concurrently capturing an entire patient image. In another aspect of the present invention, the pressurized chamber is an air mattress and at least one of the non-targets comprises a bed sheet placed between the target and the one or more detectors.

In one embodiment the present invention is a method for noninvasive measurement of a target versus a non-target, comprising the steps of: (i) illuminating a target with two or more light sources each of the light sources having a defined emission spectra and angle; (ii) capturing one or more images with one or more detectors positioned to capture light from a target, the images comprising one or more two dimensional spatial images of the target; and (iii) calculating a transform of the time variations of the at least a portion of the spatial images to distinguish between target and non-target image information based on differing frequency behaviors.

In one aspect of the detection method of the present invention the transform of the time variations of at least a portion of the spatial image information is a discrete Fourier transform. In another aspect of the detection method of the present invention, wherein the processor further calculates a transform of at least a portion of the spatial image information to further distinguish between target and non-target image information based on differing inverse spatial behaviors. In yet another aspect of the detection method the position, orientation and intensity of light sources are selected to reduce or eliminate specular reflectance. In a further aspect of the detection method of the present invention, the target is suspected of having a decubitus ulcer or precursor thereof.

In one aspect the method of the present invention further comprises: (i) one or more distance standards positioned at a known distance from the detector, (ii) one or more intensity references standard positioned to diffusely reflect light from the light sources into the detector to calibrate the detector, (iii) one or more object references positioned to diffusely reflect light from the light sources into the detector to calibrate the detector.

In another aspect of the present invention the two or more light sources comprise light emitting diodes under control of the processor, wherein the processor can individually trigger each of the light emitting diodes. In a further aspect the one or more light sources and the one or more detectors are on planes nearly parallel to the target surface. In yet another aspect the processor further detects the interface between target and non-target portions of an image captured by the detector. In a further aspect of the present invention the two or more light sources and the one or more detectors are positioned in a pressurizable chamber to illuminate the target surface, wherein the pressure within the chamber is controlled by the processor.

In one aspect the processor can calculate when a portion of the image of the target is close to a preset level that correlated with a known target and can trigger an alarm on the detection of one or more of the following parameters: a change in surface conditions, movement, moisture, temperature changes, a solid object, a liquid, and oxygenation changes.

In another aspect, the processor triggers an alarm on the detection of a change in the parameter of a non-target, the presence of a non-target, and the absence of a previously present non-target, or movement of a target or non-target. The processor can detect a non-target including: a mattress, a mattress cover, a sheet, a jewelry, a bandage, an outline of a patient or a fluid by taking any of continuous and semi-continuous measurements and using time based information and trends to perform various functions, comprising any of: estimation of precision, estimation of confidence intervals, and prediction of future events.

In yet another aspect the method described in the present invention further comprises: (i) one or more sources of background light, and (ii) a patient support in a pressurized chamber capable of moving the target in two or three dimensions. The patient support and apparatus capable of capturing an entire patient image in one or more target images. In a further aspect of the present invention the two or more light sources and detectors comprise part of an array of imaging modules, each module comprising the apparatus, wherein each of the imaging modules is capable of concurrently capturing an entire patient image. In another aspect, the processor is programmed with a predetermined set of positions for a target support, wherein deformations of the target support cause one or more specular reflections that saturate the detector, wherein the processor turns off one or more light sources within an array of light sources that cause specular reflections of the target support.

In another embodiment the present invention describes a method for noninvasive measurement of a target versus a non-target, comprising: (i) illuminating a target with two or more light sources each of the light sources having a defined emission spectra and angle; (ii) capturing one or more images with one or more detectors positioned to capture a target reflection, the images comprising one or more two dimensional spatial images of the target; and (iii) calculating a transform of at least a portion of the one or more spatial images to distinguish between a target portion and a non-target portion in the two dimensional spatial images based on differing inverse spatial behaviors between the target and the non-target. The target for detection using the method described in the present invention is suspected of being a decubitus ulcer or precursor thereof.

In yet another embodiment the present invention is an apparatus for noninvasive measurement of physiological conditions of a tissue, comprising: (i) a base comprising two or more arrays, each array comprising two or more light sources with each of the light sources having a defined emission spectra and angle of illumination, and one or more detectors positioned to receive light from the skin; (ii) a processor in communication with the one or more detectors, wherein the processor calculates a transform of at least a portion of the one or more spatial images to distinguish between a target portion and a non-target portion in the two dimensional spatial images based on differing inverse spatial behaviors between a target and a non-target; and (iii) an input/output module connected to the processor that provides optical and/or electrical signals between the base module and a source of electrical power for the processor, the light sources and the detectors.

In a further embodiment the apparatus of the present invention is utilized for noninvasive measurement of physiological conditions on the surface of the skin, and comprises: (i) a base comprising two or more arrays, each array comprising two or more light sources with each of the light sources having a defined emission spectra and angle of illumination, and one or more detectors positioned to receive light from the skin, wherein the light source emission angles are selected to optimize the amount of light that is transmitted through an interface between the light array and the skin, while minimizing the light that is reflected off of the surface that would be directly incident on the detector; (ii) a processor in communication with the light sources and one or more detectors, wherein the processor calculates a transform of the time variations of the at least a portion of the spatial images to distinguish between target and non-target image information based on differing frequency behaviors; and (iii) an input/output module connected to the processor that provides optical and/or electrical signals between the base module and a source of electrical power for the processor, the light sources and the detectors.

In another embodiment the present invention comprises a system for noninvasive measurement of physiological conditions on the surface of the skin, wherein the target is a human patient comprising: (i) a base comprising two or more arrays, each array comprising two or more light sources with each of the light sources having a defined emission spectra and angle of illumination, and one or more detectors positioned to receive light from the skin, wherein the light source emission spectra and angle of illumination are selected to optimize the amount of light that is transmitted through an interface between the light array and the skin, while minimizing the light that is reflected off of the surface that would be directly incident on the detector; and (ii) a processor in communication with the light sources and one or more detectors, wherein the processor calculates a transform of the time variations of the at least a portion of the spatial images to distinguish between target and non-target image information based on differing frequency behaviors; wherein the processor can trigger an alarm if the processor detects a change in a parameter of a non-target, the presence of a non-target, absence of a previously present non-target, or movement of a target or non-target, including: a change in surface conditions, movement, moisture, temperature changes, a solid object, a liquid, and oxygenation changes and the processor can detect a non-target including: a mattress, a mattress cover, a sheet, a wedding ring, an outline of a patient or a fluid.

In a further embodiment the present invention is a system for noninvasive evaluation of a target versus a non-target on a living target, comprising: (i) two or more light sources directed at the target; (ii) one or more detectors positioned to capture light reflected from the target comprising one or more two dimensional spatial images of the target; (iii) a processor in communication with the detectors, wherein the processor calculates a transform of the time variations of the at least a portion of the spatial images to distinguish between target and non-target image information based on differing frequency behaviors, wherein the living background values in the spatial images of the target are separated from non-target values, and (iii) generating an image that shows where non-targets are located at or about the surface of the human body or in between the human body and an item of clothing.

In one aspect the processor in the system of the present invention can trigger an alarm if the processor detects a change in a parameter of a non-target, the presence of a non-target, absence of a previously present non-target, or movement of a target or non-target. In a further aspect the processor in the system of the present invention can detect a non-target including: a weapon, a metal, a plastic, a cloth or a container.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
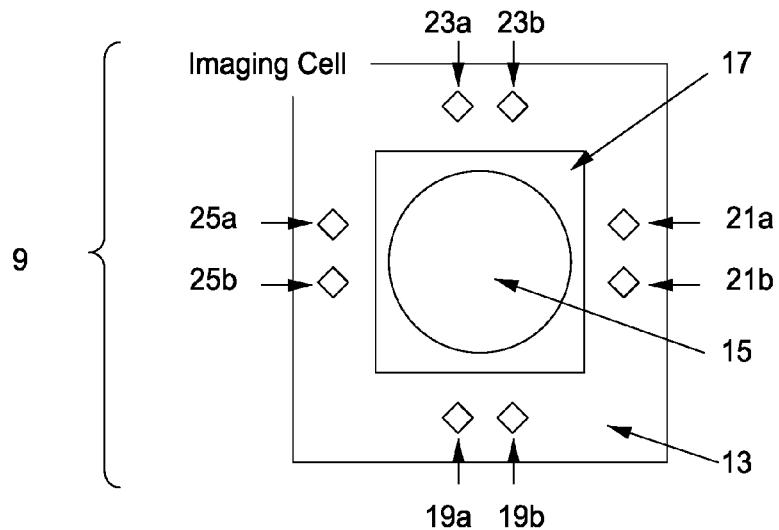
FIG. 1A shows the top view of an imaging cell, comprising a light source (one or more light emitting diodes), a lens, an imaging chip, and a PCB for providing mechanical and electrical support on which the imaging chip is mounted.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Decubitus ulcers are a growing problem in hospitals and extended care units as ill patients with compromised health are more prone to skin and tissue degeneration. In light of such concerns, nurses are trained to maintain the skin integrity and check for the formation of such ulcers. Nevertheless, in the multitude of concerns a nurse keeps in mind, many of these issues cannot be tended to. Specialty mattresses are now available that redistribute pressure along predetermined sequences, random patterns or based upon pressure measurements. Nevertheless, it is well known that pressure is a necessary but not sufficient condition for the formation of decubitus ulcers. Therefore, a system that can detect changes in the perfusion to a specific area can eliminate the need for nurses to do constant physical checks and improve the performance of pressure redistribution mattress systems. Rather, once the system detects a troublesome area, such as where insufficient perfusion is occurring or a fluid is present underneath the patient, the nurse can be alerted to check the area and reposition the patient according to clinical care protocols or the mattress itself can readjust the patient's position while the resulting impact on perfusion can be confirmed.

The present invention is a multi-wavelength imager that can be utilized for monitoring and diagnostic purposes in a health care or home care setting. The invention includes the imaging cell, electro-mechanical grid connector, and interfacing mechanism with existing standard hospital beds. Each imaging cell contains at least one light source emitting light about a specific wavelength (e.g. LED or Laser). Each LED (light-emitting diode) functions as either a reference wavelength or a wavelength providing diagnostic information of the patient's skin or vascular condition. The detector picks up the light from the patient (that has traveled through non-biological materials such as a window or a mattress), this chip camera converts the light signal into a digital image via an array of photodetectors (e.g. CMOS or CCD). It is also possible to use a single element detector and create an image with a scan able light source or movable stage.

Examples of photodetectors for use with the present invention are available from commercial sources. For example the IM103 CMOS image sensor available from Sensata Technologies having VGA resolution (640×480) and is capable of detecting both visible and near-infrared wavelengths. Another example is the TC922 CMOS image sensor available from Texas Instruments Incorporated having SVGA resolution (800×600) and containing a high response amplifier in the pixel and reset noise reduction circuit that provides high sensitivity and high signal to noise ratios. The ICX418ALB CCD solid-state image sensor 811 (H)×508 (V) from Sony is also another example, having a diagonal 8 mm (type ½) system featuring a field period readout system and an electronic shutter with variable charge-storage time.

Ideally the detector is positioned so as to minimize the collection of light that is "reflected" in a perfect way ("specular" reflection). In other words, that the angle of reflection is equal to the angle of incidence. The reason for this is that a large amount of light may be reflected in this way when compared to the light that is "diffusely" reflected, or that effectively comes back out from the target at a large distribution of angles.

Light sources used in the present invention can be an IR light source such as the LI521 LED manufactured by Seoul Semiconductor Co., Ltd. using a GaAlAs/GaAs semiconductor chip and having a typical radiant intensity of 120 mW/sr, peak wavelength of 870 nm and packaged so as to have a view angle of 20°, or the OPE5588 GaAlAs IR emitter optimized for emission at 880 nm and packaged in an industry standard T1¾ plastic package with lens and cup frame having a typical radiant intensity of 60 mW/sr, half angle of +/−10°, typical rise time of 1.5 microseconds and typical fall time of 0.8 microseconds. Other examples of red light sources may include a LED such as the LR340 manufactured by Seoul Semiconductor Co., LTD. having a typical luminous intensity of 450 mcd, peak wavelength of 641 nm and packaged in a 3 mm type package with a transparent epoxy lens so as to have a view angle of 44°, or the OPA6625 manufactured by Knowledge*On Inc. having a typical brightness of 1100 mcd, typical emission at 660 nm and packaged in an industry standard T1¾ plastic package.

A light source assembly other than a LED can be used in the present invention, if it can provide a substantially monochromatic light (e.g. a laser or a broad band light source with a filter), or a desired combination of light wavelengths, and provided that the light source can be turned on and off fast enough for the images to be captured without the inclusion of the transients in the subsequent frames.

The module casing material of the present invention must be durable and be preferably made of a light weight material that is internally finished in black matte so as to minimize unwanted reflections from the module casing. The material is preferably made of a plastic material which can be readily formed by injection molding and made absorbing through the incorporation of dyes within the plastic.

While the multi-wavelength imager can provide a seamless solution for the growing issue of pressure ulcers it can simultaneously provide information regarding perfusion and appropriate blood flow to certain body parts, which are important when considering the care of trauma patients and the elderly, as well as the healing of infections, wounds, and amputation sites. By providing a complete image overview of the patient, the healthcare provider can gain an understanding of where the source of the problem is and treat it accordingly before the problem becomes visible and more severe. Additionally, part of the invention lies in determining the importance of different wavelengths outside of the ones currently in use by pulse oximeter machines.

Current hyperspectral imagers typically utilize spectrometers to acquire images at a large number of wavelengths; however, in the present invention discrete light sources are selected based upon the most relevant wavelengths relating to the physiology of interest for the patient and additionally to serve as references—thus allowing for a cost-effective solution. Due to the cheaper solution, the imager can be placed in each cell of the grid to provide a complete patient overview. Since the system can use, e.g., a limited set of wavelengths (or emission spectra), the time required for acquiring a complete image set is far less than a typical hyperspectral imaging system. By determining the set of emission spectra providing the most clinically valuable information, the extra time required for typical hyperspectral imaging is avoided. Also, image samples may be taken at all the wavelengths of interest multiple times during the beat of a human heart, thus allowing the frequency analysis of the time variations of the oxygenated hemoglobin. The proposed invention, while simplifying new hyperspectral technologies, takes existing reflectance technologies (pulse oximeters) in critical care to a more meaningful level. Rather than providing average information on oxygen saturation about a specific area within the patient, this system may provide a complete body image of the patient's perfusion and oxygen saturation status particularly on unexposed surfaces and without physical contact of the device with the patient, which is important so as to not contribute to the formation of, e.g., decubitus ulcers. For example, the images can be processed further to calculates a transform of the time variations of at least a portion of the spatial images to distinguish between target and non-target image information to measure the presence of one or more factors that lead to changes in tissue health selected from decubitus ulcers, cancerous lesions, skin transfers, skin temperature, skin oxygenation, burns, skin trauma, skin diseases, autoinflammatory diseases, autoimmune diseases, infectious diseases, and combinations thereof.

Skin grafting is a common reconstructive surgical technique utilized for the treatment of compromised skin due to cancer, ulcers, burns or cosmetics. Skin or tissue flaps are alternatives where the blood supply is maintained or reestablished because the donor area does not have the required vasculature to sustain a skin graft. They can be either of the free flap or pedicle flap varieties. Free flaps are flaps completely extracted from the donor site and reattached to the recipient site via microsurgery which joins small arteries and veins using an operating microscope. Pedicle flaps use an existing muscle which maintains the blood and nerve supply to it, from which it is mobilized and/or twisted to cover an adjacent area that has been removed. The base of a pedicle flap is a distance away from the recipient site. More recent innovations involve cadaveric allograft, porcine xenograft, and bioengineered skin [5]. Despite the pervasive use of skin replacement procedures, advancements in the monitoring and management of the healing processes have been relatively modest, while delayed detection of failed tissue transfers results in significantly higher care costs and patient hardships.

It is well known that insufficient arterial flow to a flap and/or poor venous outflow often leads to failed outcomes. Related visual indicators include skin color, capillary refill and turgor [2]. Though studies have reported some successes in correlating monitoring device data with transplantation healing outcomes based on both invasive and non-invasive approaches, these systems have either been awkward to use or limited in applicability [1,2]. Hence monitoring of healing is still largely performed visually by the trained dermatologic clinician. The present invention provides a safe and effective, easy-to-use imaging device for the real time assessment of skin graft or flap healing.

A particular monitoring approach that has recently shown significant potential in wound healing is multi-, or hyper-, spectral imaging. Payette et al. demonstrated encouraging results suggesting that maps of oxygen saturation determined from spectral images appeared to provide early indication of skin flap failure [1]. Leonardi et al. applied a spectral imaging system to burn injuries finding significant correlations with burn severity and effectiveness of healing [6]. Palero et al. performed tissue spectral imaging to show visualization of tissue morphology and the clear identification of tissue layers in rats, but clearly stated that their system could only penetrate 0.1 mm beneath the skin, or up to the basal layer [7]. Stamatus et al. focused on water and hemoglobin absorption bands to show the feasibility of imaging aspects of an edema reaction in vivo [8]. Kerekesa et al. described a 4 M pixel imaging system with 30 wavelength resolution, yet utilized it only to show static oxygenation data maps in the near surface of the skin [9].

Collectively, these recent papers are representative of the fundamental limitations of existing spectral imaging approaches. Specifically, the applicability of reported spectral imaging systems for tissue assessment is limited by the relatively shallow depth that may be imaged (1-2 mm) [3]. Furthermore, existing spectral imaging systems gather data over several seconds or even minutes, thus, completely overlooking the dynamic aspects of blood flow throughout the cardiac cycle that include important information with respect to hemodynamic pathology. Finally, due to the need for investigator intervention, data analysis is normally done after a full set of image cubes are taken, hence providing analysis outcomes well after the events have occurred [10]. Restated, the specific technical problems to be addressed are: (1) depth of spectral images, (2) time to capture images at relevant wavelengths, and (3) time to analyze data.

The ability to use this system in any hospital bed (regardless of manufacturer), allows both an ease of implementation and cost effectiveness unmatched by other spectral imagers currently in existence. Additionally, each imaging unit can be placed in any area of the grid—therefore if all units are not required, the healthcare provider has the option to alter such spatial configurations. Alternatively, a single unit may be located in a clinician's office so as to facilitate the rapid evaluation of only a portion of the patient's body. Overall, the proposed invention provides a cost-effective, efficient, and clinically valuable solution in a flexible and useful manner in light of health care demands. Each imaging unit would provide a large scale area of information (16-144 in$^2$) and combined into the array configuration creates an overall image of the perfusion and vascular status of the patient. In contrast to hyperspectral imaging systems currently being researched, the multi-wavelength imager provides data for a limited set of wavelengths that are clinically useful on a time scale that allows for dynamic visualization of blood flow and perfusion. Additionally, the proposed system scans across a larger area in comparison to the majority of current medical hyperspectral imaging systems, which deal with either very focused areas or microscopic areas as seen in microbiology and pathology applications.

To reduce the effects of ambient and stray light, each cell is housed in an absorbing enclosure with raised sides to ensure that primarily only light from the source reflected from the sample hits the detector. This electronic signal is relayed to the computer via the electro-mechanical grid that serves as both the mechanical and electrical support structure for the imager array.

The following diagrams illustrate the technology invented and subsequent explanation of each component of the invention.

FIG. 1A is a representation of an imaging cell 9. Imaging cell 9, has an imaging chip 17, that comprises a lens 15. The imaging chip is surrounded by light sources or LEDs, 19a, 19b, 21a, 21b, 23a, 23b, 25a, and 25b. The imaging chip 17, and the LEDs, 19a, 19b, 21a, 21b, 23a, 23b, 25a, and 25b are mounted on a printed circuit board (PCB) 13. Furthermore, a digital signal processor and memory may be incorporated on each PCB to facilitate local signal processing and reduce the amount of data sent to a remote computer).

Figure 1B:
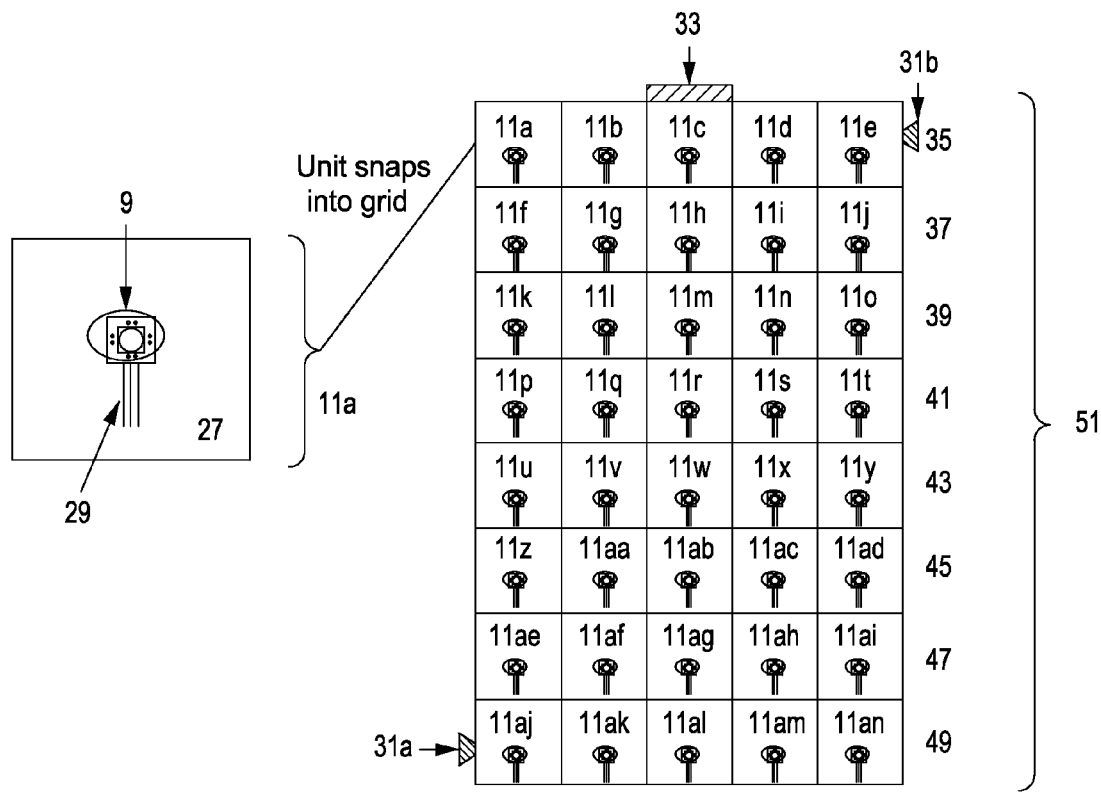
FIG. 1B depicts a 5×8 imager array with electrical and PC connections. The imager array has 40 imaging units, snapped on to the grid surface.

FIG. 1B is a diagram of an imaging super-array 51 (the number of total units required is a function of the application). Super-array 51 as shown in FIG. 1B is 5×8 grid comprising of 40 units (11a-11an). Each unit comprises of an imaging cell similar to 9 (as described in FIG. 1A), mounted on a mechanical support 27 and has electrical contacts 29 at the back. The back of each imaging cell unit (for e.g. 11a) snaps into the grid of the super array 51. The signal from the super-array is transmitted from each individual grid to the PC via standard connections 31a and 31b located on the grid. In addition to the PC connection, outlet power 33 is available on both sides of the grid to maintain flexibility in the patient environment. The arrangement of each unit within the grid is also flexible (the number of units and spatial relationship can be altered according to the needs of the patient). The super-array grid 51, described in FIG. 1B has forty units distributed over eight rows 35, 37, 39, 41, 43, 45, 47, and 49. Row 35 has units 11a, 11b, 11c, 11d, and 11e. Row 37 has units 11f, 11g, 11h, 11i, and 11j. Row 39 has units 11k, 11l, 11m, 11n, and 11o. Row 41 has units 11p, 11q, 11r, 11s, and 11t. Row 43 has units 11u, 11v, 11w, 11x, and 11y. Row 45 has units 11z, 11aa, 11ab, 11ac, and 11ad. Row 47 has units 11ae, 11af, 11ag, 11ah, and 11ai. Finally, row 49 has units 11aj, 11ak, 11al, 11am, and 11an.

Figure 1C:
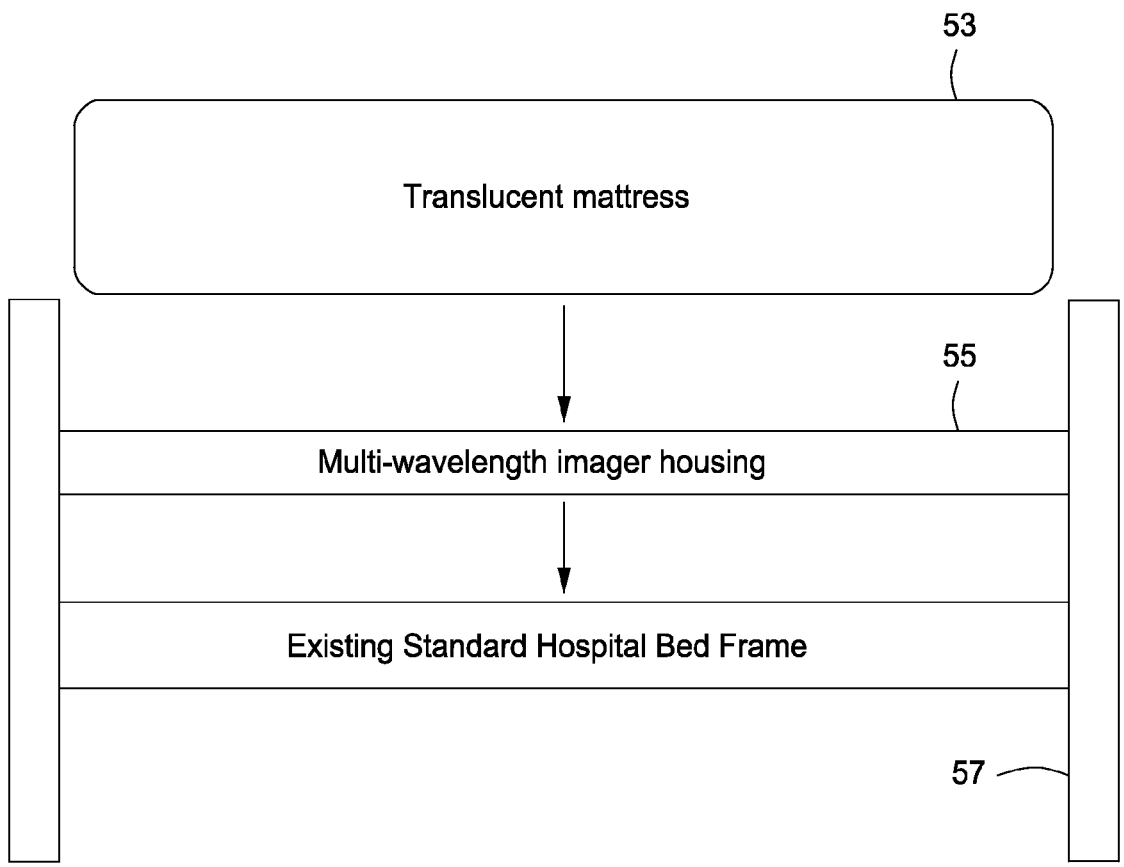
FIG. 1C shows an image of an imager array/housing that is integrated with a standard hospital bed.

The housing may conform to the standard hospital bed sizes used in current health care environments, thus allowing for the immediate use of such technologies. FIG. 1C represents the application of the present invention in a hospital/clinical setting. The housing 55 is simply placed on the bed frame 57, beneath the mattress 53 prior to the transfer of the patient onto that bed. From there, all access points required for the utilization of the imager 55 would be located on the side of the array allowing easy access for nurses and physicians.

Figure 2A:
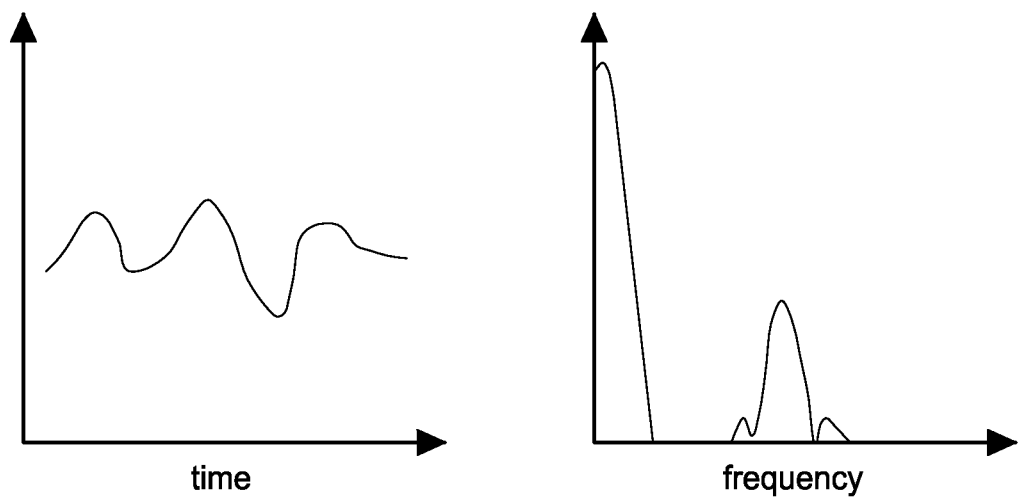
FIG. 2A describes the time varying signals that have different frequency behaviors of the time dependent signal for the target and the non-target.
Figure 2B:
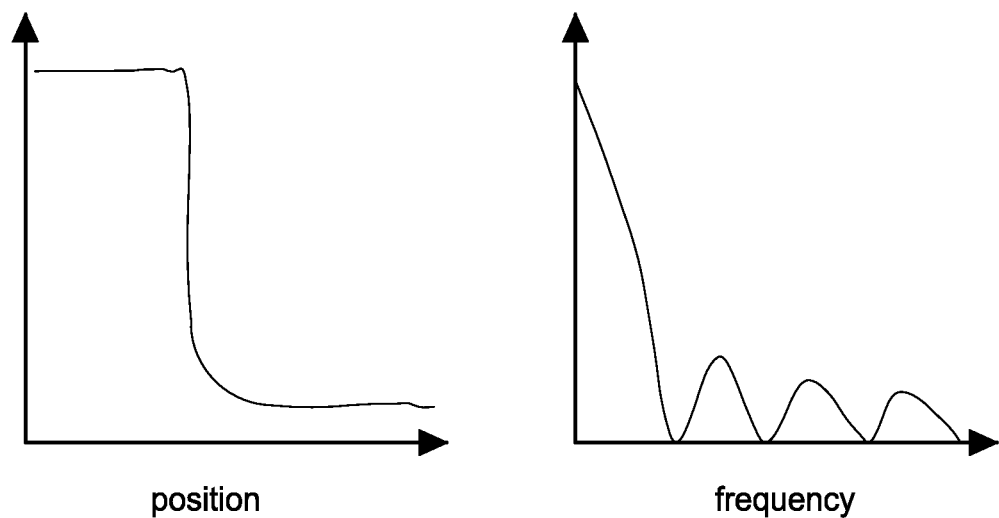
FIG. 2B describes the spatially varying signals that have different frequency behaviors of the spatially dependent signal for the target and the non-target.

FIG. 2A describes the time varying signals that have different frequency behaviors of the time dependent signal for the target and the non-target. FIG. 2B describes the spatially varying signals that have different frequency behaviors of the spatially dependent signal for the target and the non-target.

Care environments will use a variety of room lights. The contribution of this lighting below the patient is limited because the patient does not generally transmit this light. However, there is also a beneficial affect in that the image generated by the contrast of the areas where the patient is blocking the background light and where they are not, can provide an indication as to where the patient is located. Typical room lighting is powered by AC power sources with time varying components such as 60 Hz which often result in an AC component within the illumination of the room light of similar frequency. Since frequencies characteristic of blood perfusion and pulsatile flow are typically less than 2.5 Hz, the contributions of these AC signal components can readily be distinguished in the frequency domain and thus do not interfere with the present invention.

Figure 2C:
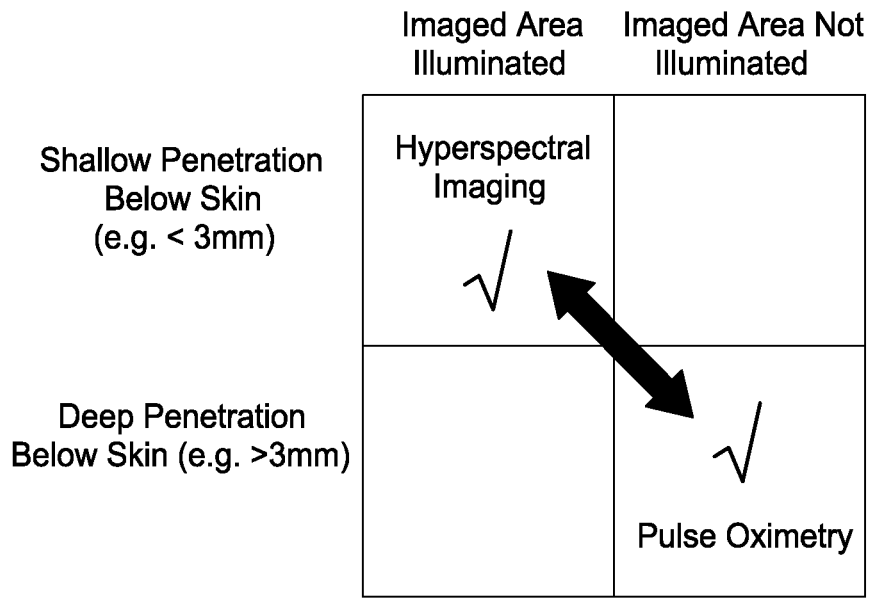
FIG. 2C shows the controlled illumination varying the displacement distance of injected light from imaged surface and the displacement pattern.

FIG. 2C shows the controlled illumination varying the displacement distance of injected light from imaged surface and the displacement pattern results in images that are sensitive to differing penetration depths and regions below the skin.

Figure 2D:
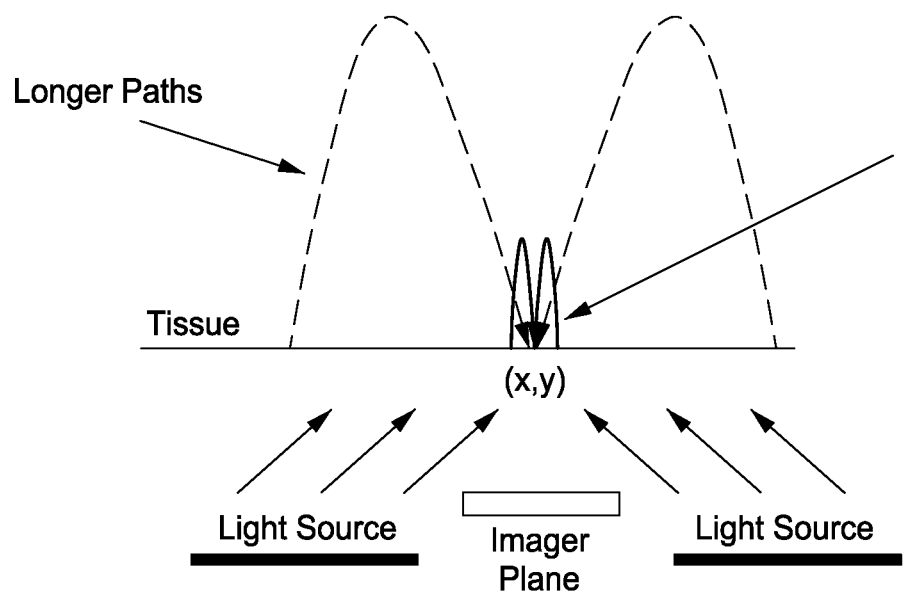
FIG. 2D shows the coincident illumination and imaging of the Prior Art.

FIG. 2D shows the coincident illumination and imaging used with common prior art multi-wavelength or hyperspectral imaging systems illumination locations coincide with imaging locations at a given point (x,y). The skilled artisan will recognize that the present invention can be used in systems that are not limited to systems that depend on time variations, but can be applied to earlier images (including standard images). The photons re-emitted at the imager from location (x,y) are a combination of information from various light injection locations and resulting sampling paths. However, longer paths generally result in much larger losses. As a result, an image containing collected photons from location (x,y) predominantly represents shallow and narrow areas within the tissue. The latter is confirmed in the literature with Monte Carlo simulations by Binzoni T, Vogel A, Gandjbakhche A H, Marchesini R, "Detection limits of multi-spectral optical imaging under the skin surface," Phys. Med. Biol. 53, 617-636, 2008. In this embodiment, the image acquired is a reflection of the super majority of photons injected about (x,y) are subsequently re-emitted at (x,y) having interacted with a narrow and shallow region of the skin.

Figure 2E:
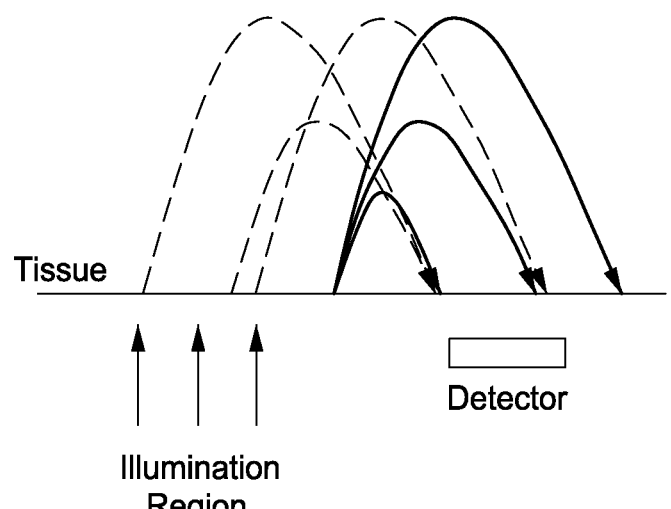
FIG. 2E shows the asymmetric illumination and imaging of the Prior Art.

FIG. 2E shows an example of asymmetric illumination and imaging of the prior art, which is used for multi-wavelength monitoring devices such as reflectance mode pulse oximeters utilize asymmetric and fixed displacement illumination locations. As such an image at point (x,y) is a combination of information from various sampling paths that represent a fixed combination of depth contributions and are furthermore laterally displaced from the image point.

Figure 2F:
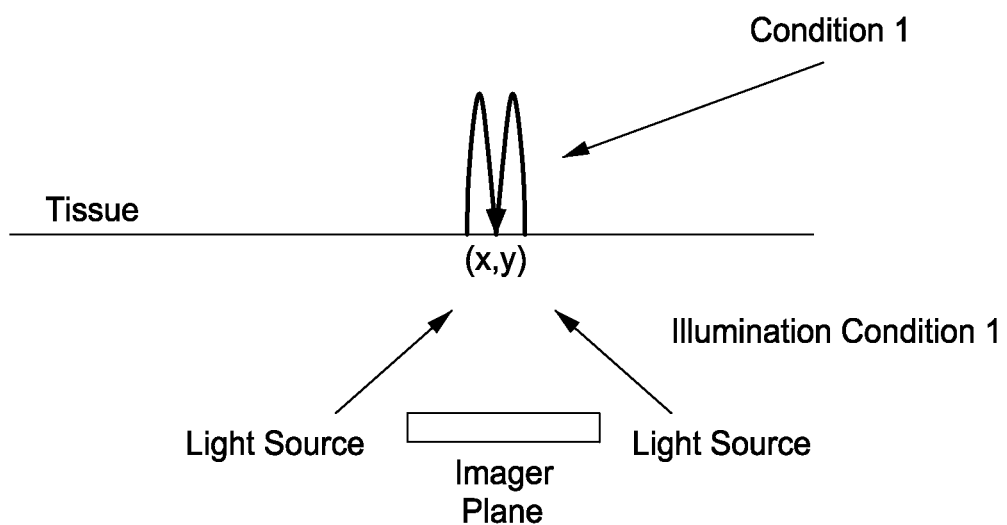
FIG. 2F demonstrates the variable displacement illumination of the present invention.

FIG. 2F shows graphically the variable displacement illumination embodiment of the present invention, which makes it possible to resolve images as a function of depth into the tissue by varying the illumination locations as a function of distance from a given (x,y) point to be imaged and also by use of symmetry variations.

Figure 2G:
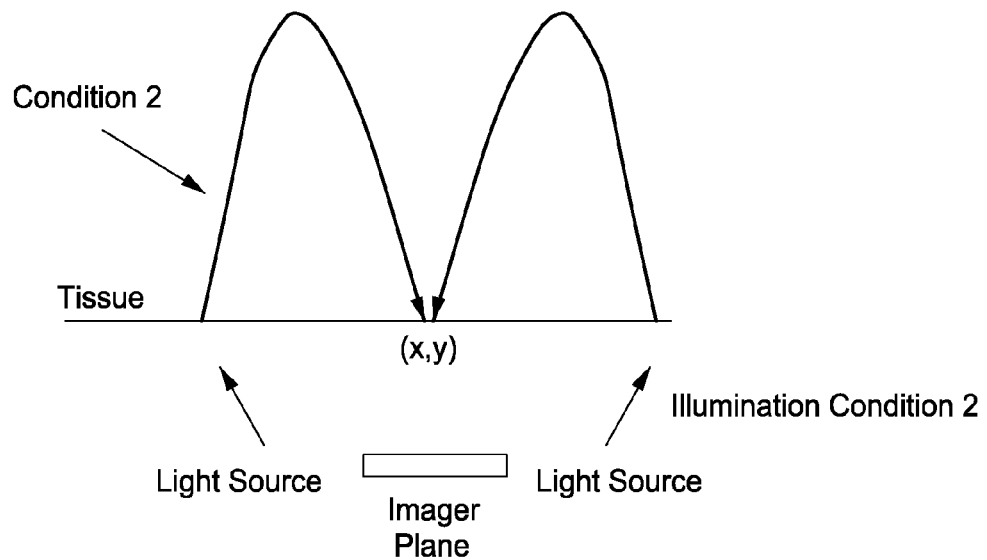
FIG. 2G shows another example of the variable displacement illumination of the present invention.

FIG. 2G shows graphically another variable displacement illumination embodiment of the present invention, which makes it possible to resolve images as a function of depth into the tissue by varying the illumination locations as a function of distance from a given (x,y) point to be imaged. By using a variety of patterns of alternating displacements images containing samples from differing depths and locations can then be "de-convolved" to reconstruct image slices as a function of depth into the skin. Furthermore, by utilizing conditions with no coincident illumination, the imager can then be made sensitive to photons from much deeper below the skin, in contrast to the findings and limitations of the prior art (Binzoni T, Vogel A, Gandjbakhche A H, Marchesini R, Detection limits of multi-spectral optical imaging under the skin surface, Phys. Med. Biol. 53, 617-636, 2008.).

Figure 2H:
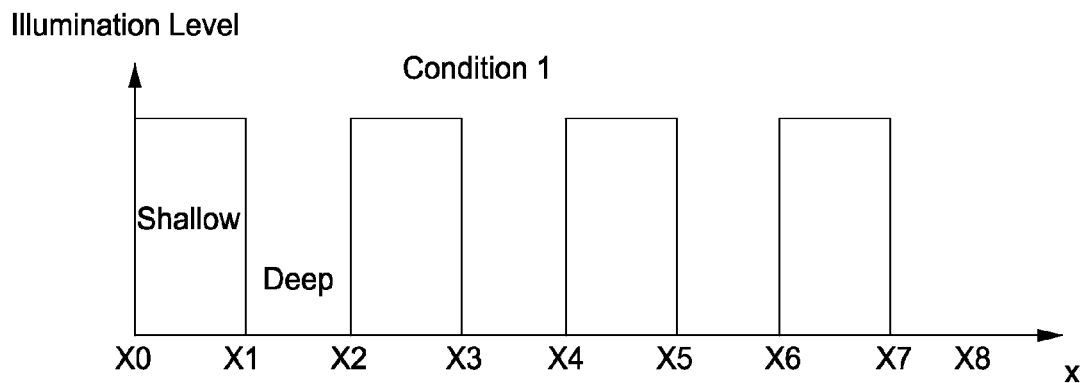
FIG. 2H shows another example of the depth resolved imaging and illumination illumination of the present invention.
Figure 2H:

FIG. 2H shows the signal for the image captured under illumination condition 1 contains both deep and shallow information. The offset illumination condition 2 contains the shallow and deep information at locations missing from condition 1. In this way the images may be separated to create new images having only shallow and deep information.

Figure 3A:
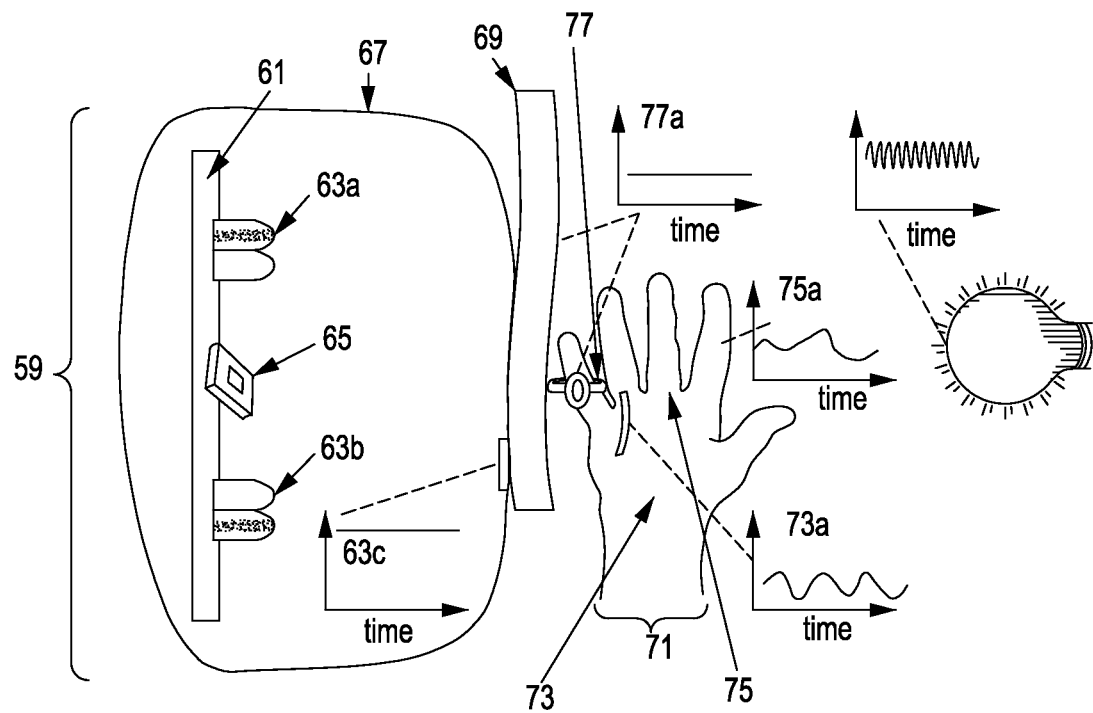
FIG. 3A is the adaptation of the present invention depicting the time variations shown by the target (a portion of the body like the palm of the hand) and the non-targets which could be piece of jewelry (for e.g. a ring), non-hand, a sheet, a container, etc.

FIG. 3A is an adaptation of the present invention for detecting a target versus a non-target based on time variations. The imager of the present invention 59 comprises a support 61, light sources 63a and 63b, and a detector 65. The imager is enclosed in a housing 67 and has a top cover sheet 69 that also is a non-target. The targets are the veins in the human hand 71. The veins are present within a human hand 71 comprising a palm 73 and fingers 75 that also are non-targets in this example. An additional non-target is a ring 77, worn on the finger 75. The reference of the light sources time variation signal is shown in graph 63c. Time variations of the different parts of the target are shown in graphs 73a and 75a. Time variation of the vein in the human hand 71 is shown in graph 73a and time variation of the fingers 75 is shown in graph 75a. Time variation of the non-target 77 is shown in graph 77a.

Figure 3B:
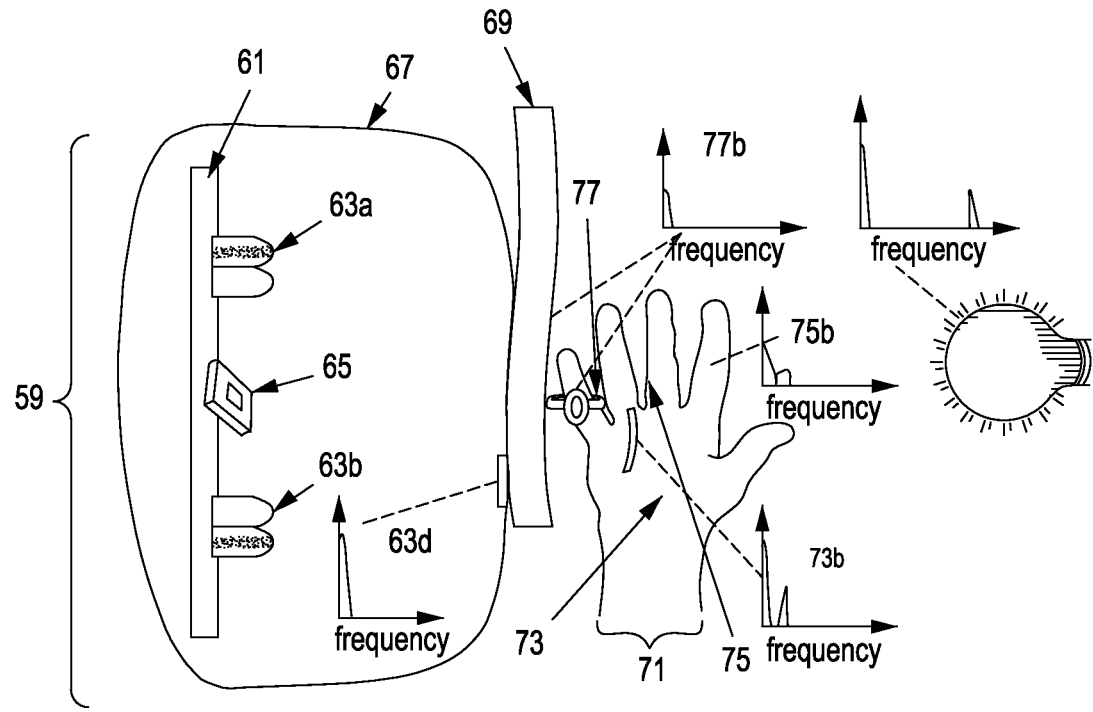
FIG. 3B is the adaptation of the present invention depicting differing frequency of time variation shown by the target (a portion of the body like the palm of the hand) and the non-targets which could be piece of jewelry (for e.g. a ring), non-hand, a sheet, a container, etc.

FIG. 3B is similar to FIG. 3A, excepting that it shows frequency variations associated with the detection of a target versus a non-target. Frequency variations associated with the background, the palm 73, the fingers 75 and the non-target (the ring) 77, are shown in graphs 63d, 73b, 75b, and 77b, respectively.

Figure 4A:
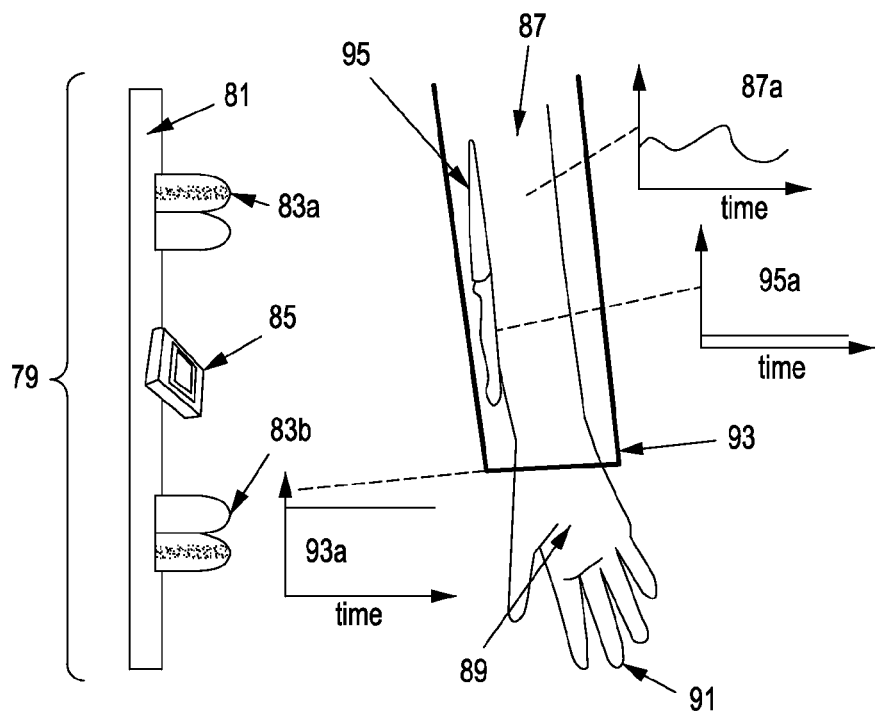
FIG. 4A is an application of the present invention for the detection of a non-target including weapons (for e.g. a knife), a metal, a plastic, a cloth or a container. Detection is based on the non-target and the target (the body) showing differing time variations.
Figure 4B:
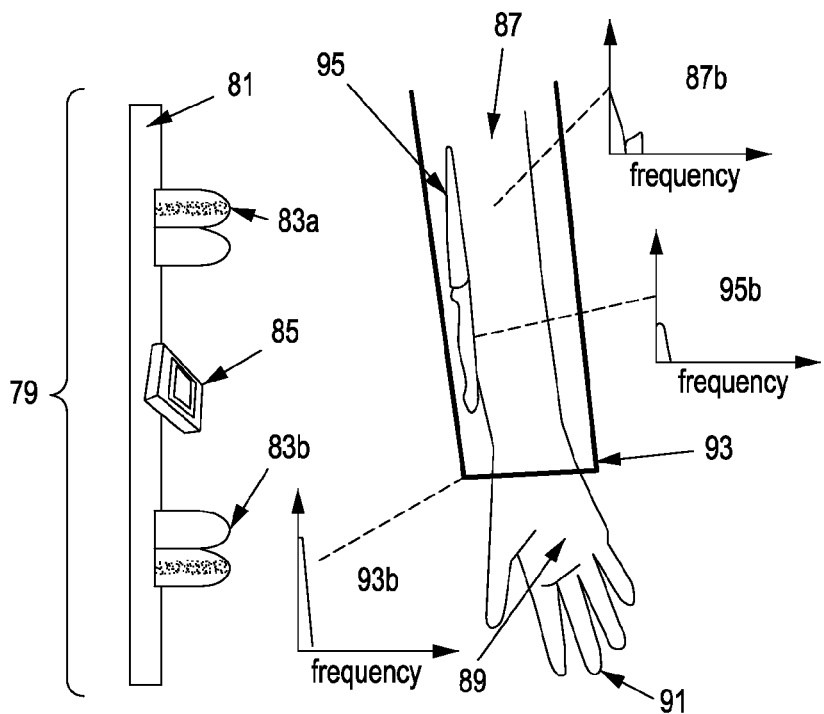
FIG. 4B is an application of the present invention for the detection of a non-target including weapons (for e.g. a knife), a metal, a plastic, a cloth or a container. Detection is based on the non-target and the target (the body) showing differing frequency variations.

FIGS. 4A and 4B describe applications of the present invention for the detection of a non-target including weapons (for e.g. a knife), a metal, a plastic, a cloth or a container based on monitoring time and frequency variations respectively. The imager of the present invention 79, comprises a solid support 81, light sources 83a and 83b and a detector 85. The target is a part of the human body comprising a forearm 87, the palm of the hand 89 and the fingers 91. The non-targets included a knife 95, concealed underneath a long shirt sleeve 93. Time and frequency variations for the target are shown in graphs 87a and 87b respectively. Time and frequency variations for the non-targets 93 and 95 are shown in graphs 93a, 93b, 95a and 95b respectively.

Figure 5A:
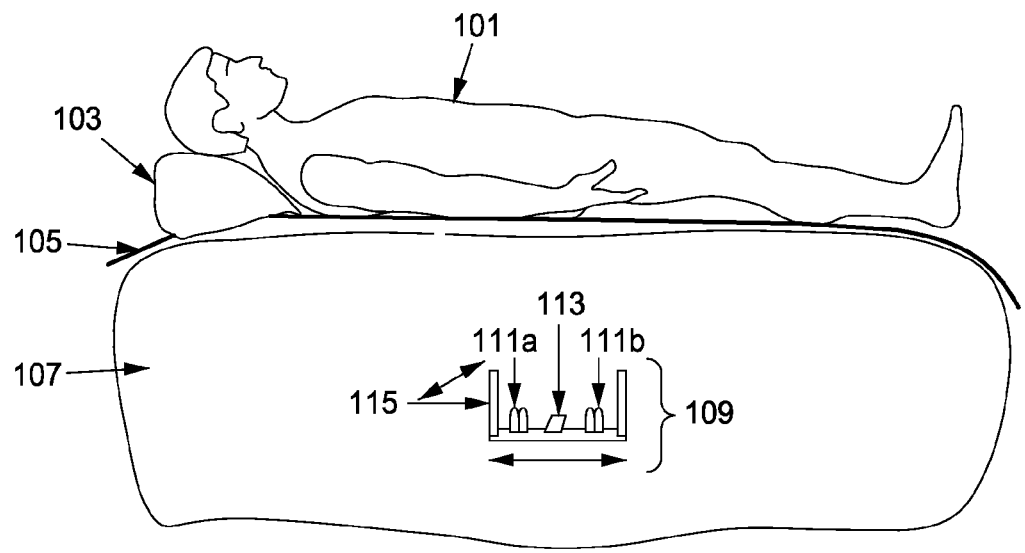
FIG. 5A shows an image of a mattress with a module. The patient is on the bed in the laying down position, and the imaging apparatus can move on a x-y stage.

FIGS. 5A-5H show different arrangements and designs of the imaging device of the present invention in different hospital settings. FIG. 5A shows an image of a mattress 107 with an embedded module 109. The patient 101 is on the bed in the laying down position, with a pillow 103 and a sheet 105 (non-target). The module 109 comprises a solid support 115, two light sources 111a and 111b, and a detector 113 all attached to the solid support 115. The imaging apparatus 109 of the present invention is capable of movement on a x-y stage.

Once the module is placed within the mattress movement on a x-y stage or a x-y-z stage would typically occur automatically based upon a predetermined program or on preset criteria in order to provide a complete image of the areas of interest or images of specific areas. In certain cases there could be a feature that would allow an operator to move the module to a specific area manually. Once information is obtained from the analysis of the imaging data that determines that the patient should be repositioned, the repositioning can be achieved by: (i) alerting clinical staff as to the location(s) of problem areas so that the course of repositioning may be determined, or (ii) by changing pressure(s) within the mattress or other properties of the mattress either automatically or manually, or (iii) by changing the position(s) of the bed and frame either automatically or manually.

Figure 5B:
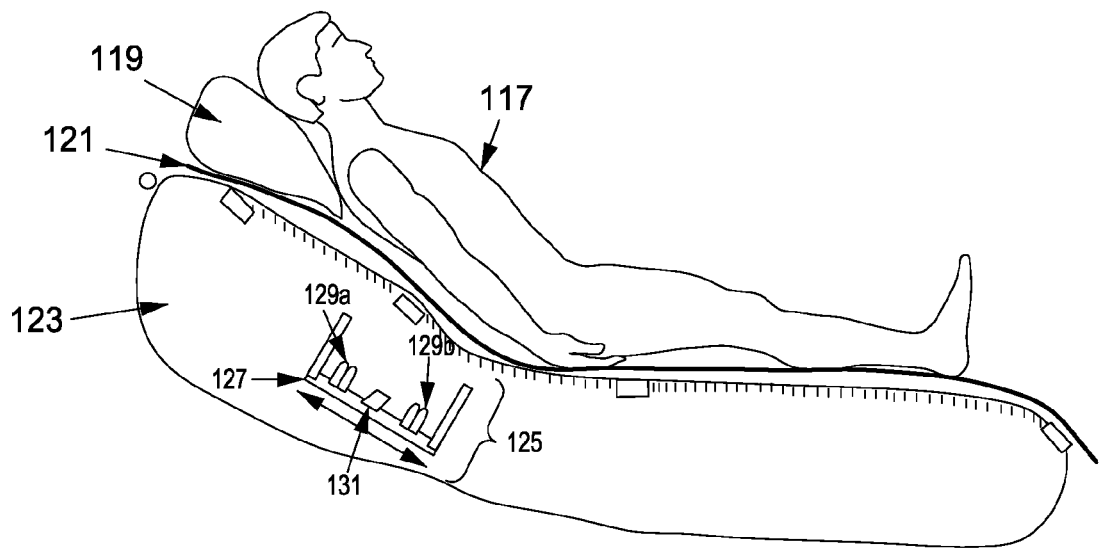
FIG. 5B shows an image of a mattress with a module. The patient is on the bed in the sitting up position, and the imaging apparatus can move on a x-y-z stage

FIG. 5B shows an image of a mattress 123 with an embedded module 125. The patient 117 is on the bed in the sitting up position, with a pillow 119 and a sheet 121 (non-target). The module 125 comprises a solid support 127, two light sources 129a and 129b, and a detector 131 all attached to the solid support 127. The imaging apparatus 125 of the present invention can move on a x-y-z stage.

Figure 5C:
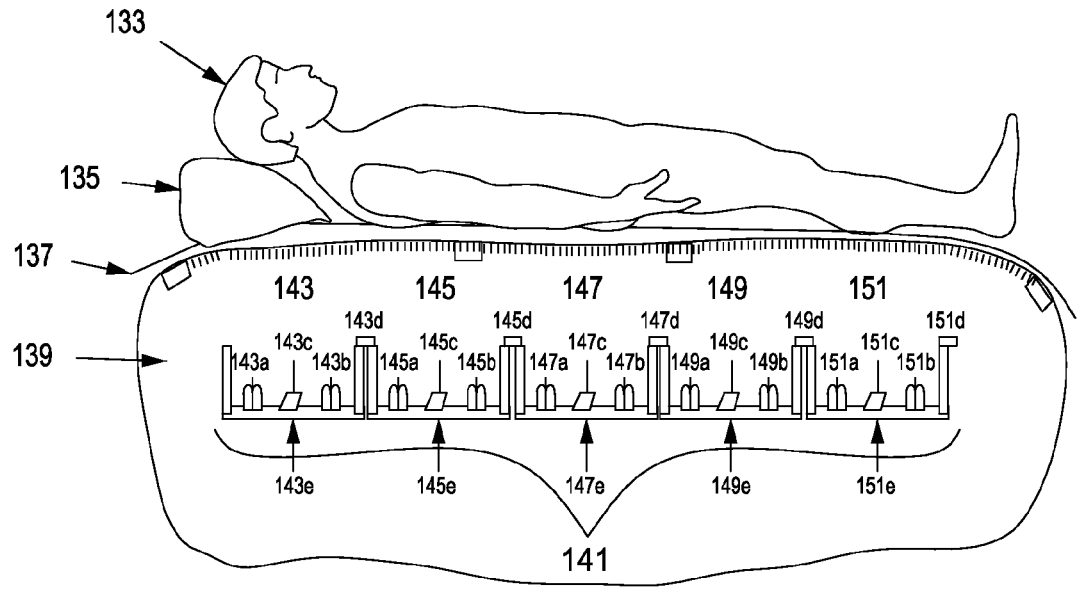
FIG. 5C shows an image of a mattress with a super array module. The patient is on the bed in the laying down position.

FIG. 5C shows an image of a mattress 139 with a super array module 141. The patient 133 is on the bed in the laying down position with a pillow 135 and a sheet 137 (non-target). The super array module comprises of five units, 143, 145, 147, 149, and 151. Each unit comprises two light sources, a detector, a solid support, and a connector connecting the adjacent units. Unit 143 has light sources 143a and 143b, a detector 143c, and a support 143e. Connector 143d connects unit 143 with unit 145. Unit 145 has light sources 145a and 145b, a detector 145c, and a support 145e. Connector 145d connects unit 145 with unit 147. Unit 147 has light sources 147a and 147b, a detector 147c, and a support 147e. Connector 147d connects unit 147 with unit 149. Unit 149 has light sources 149a and 149b, a detector 149c, and a support 149e. Connector 149d connects unit 149 with unit 151. Unit 151 has light sources 151a and 151b, a detector 151c, and a support 151e. Connector 151d is free to connect with any additional units that may be attached to the super array module.

Figure 5D:
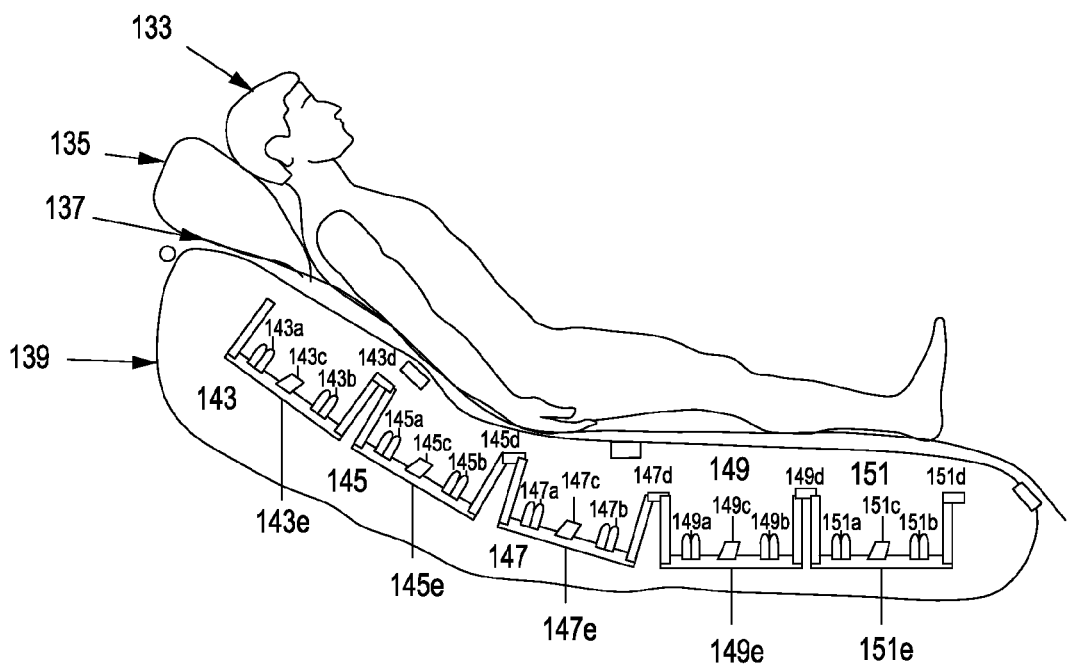
FIG. 5D shows an image of a mattress with a super array of modules. The patient is on the bed in the sitting up position, and the super array of modules is flexibly connected.

FIG. 5D is similar to FIG. 5C with the exception that the patient 133 is on the bed in the sitting up position, and the super array of modules 141 is flexibly connected. The patient 133 is on the bed in the sitting up position with a pillow 135 and a sheet 137 (non-target). The super array module comprises of five units, 143, 145, 147, 149, and 151. Each unit comprises two light sources, a detector, a solid support, and a connector connecting the adjacent units. Unit 143 has light sources 143a and 143b, a detector 143c, and a support 143e. Connector 143d connects unit 143 with unit 145. Unit 145 has light sources 145a and 145b, a detector 145c, and a support 145e. Connector 145d connects unit 145 with unit 147. Unit 147 has light sources 147a and 147b, a detector 147c, and a support 147e. Connector 147d connects unit 147 with unit 149. Unit 149 has light sources 149a and 149b, a detector 149c, and a support 149e. Connector 149d connects unit 149 with unit 151. Unit 151 has light sources 151a and 151b, a detector 151c, and a support 151e. Connector 151d is free to connect with any additional units that may be attached to the super array 141.

Figure 5E:
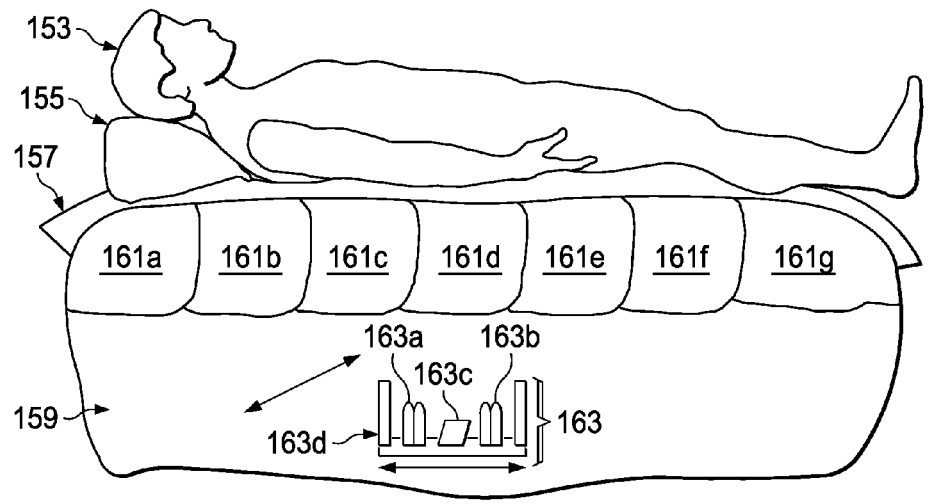
FIG. 5E shows an image of a mattress, patient, and a module in the mattress. The patient is on the bed in the laying down position, with chambers to control individual pressures. The chambers are shown with the moving apparatus, but they can be present with any configuration of modules

FIG. 5E shows an image of a mattress 159, patient 153, with a pillow 155, sheet 157 (non-target) and a module 163 in the mattress. The patient 153 is on the bed in the laying down position, with chambers 161a-161g to control individual pressures. The imaging apparatus 163 can move on a x-y-z stage, and has light sources 163a and 163b, detector 163c and a support 163d. The chambers 161a-161g are shown with the moving apparatus 163, but they can be present with any configuration of modules.

Figure 5F:
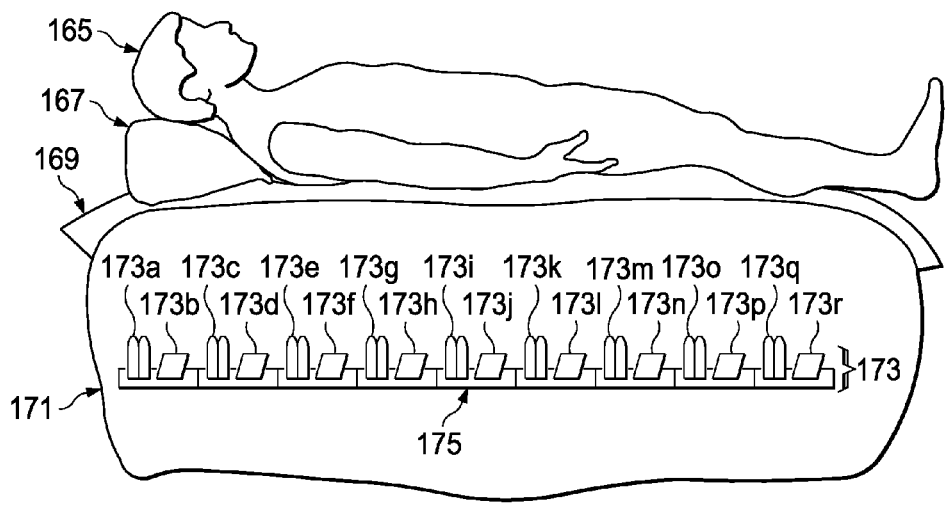
FIG. 5F shows an image of a mattress, module in the mattress, and a patient in the laying down position. The imaging apparatus is comprised of a large substrate

FIG. 5F represents a mattress 171, and a module 175 embedded in the mattress, the patient 165 with a pillow 167 and sheet 169 (non-target) is in the laying down position. The imaging apparatus 175 is comprised of a large substrate 173, having light sources 173a, 173c, 173e, 173g, 173i, 173k, 173m, 173o, and 177q and detection units 173b, 173d, 173f, 173h, 173j, 173l, 173n, 173p, and 173r attached to it.

Figure 5G:
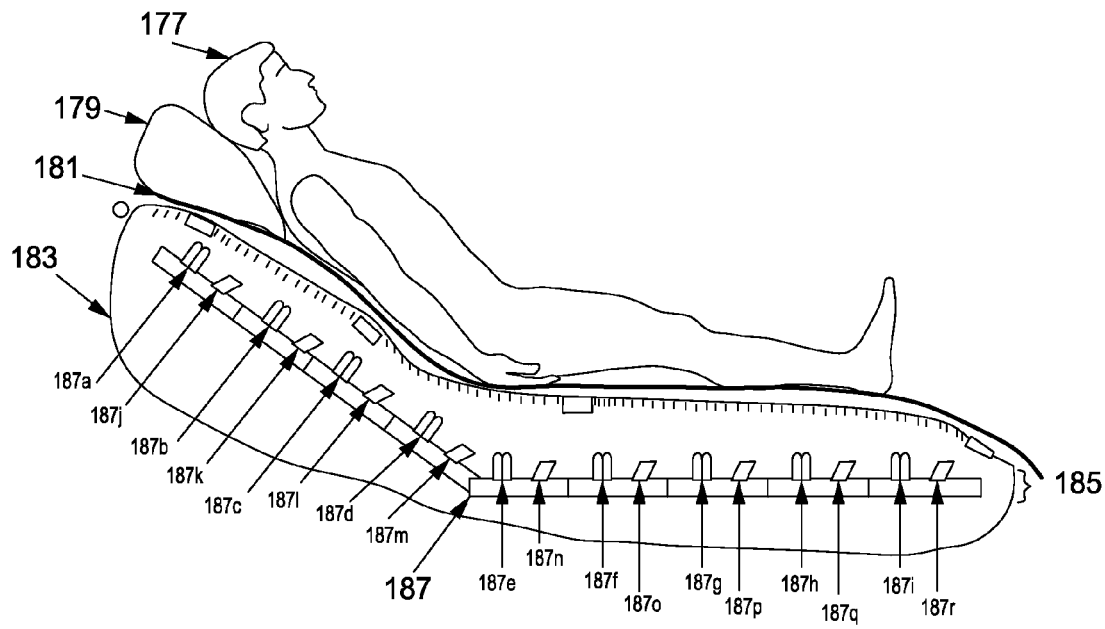
FIG. 5G shows an image of a mattress, a patient in the sitting up position, and a module in the mattress. The imaging apparatus comprised of large flexible substrate

FIG. 5G shows an image of a mattress 183, a patient 177 in the sitting up position with a pillow 179, sheet 181 (non-target), and a module 185 in the mattress. The imaging apparatus 185 is comprised of large flexible substrate 187, with light sources 187a-187i and detectors 187j-187r attached to it.

Figure 5H:
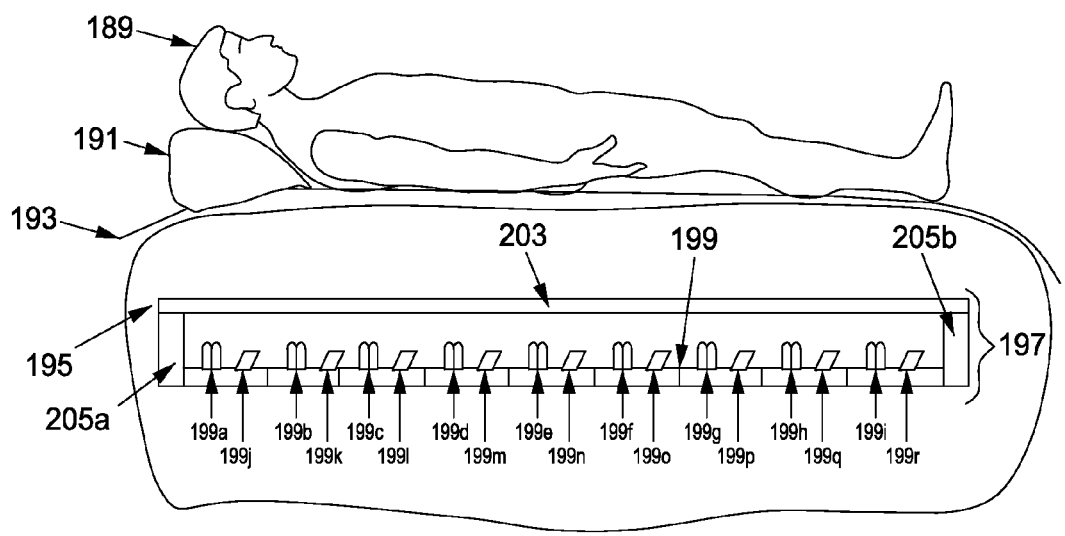
FIG. 5H shows an image of a mattress, a patient in the laying down position, and a module in the mattress. The imaging apparatus is comprised of large substrate showing intermediate CPR support structure (window, mesh, etc.).

FIG. 5H shows an image of a mattress 195, a patient 189 in the laying down position with a pillow 191, sheet 193 (non-target), and a module 197 in the mattress. The imaging apparatus 197 is comprised of large substrate 199 showing intermediate CPR support structure including a window 201, a mesh 203, and a supporting frame 205. The substrate 199 has light sources 199a-199i and detectors 199j-199r attached to it.

The module base support comprises a hard outer material for the casing which is likely to be a plastic or metal. Any material that can provide a stiff support could be used for this purpose. A Printed Circuit Board (PCB) would be affixed to the inside of the outer module casing. The PCB would likely be made of FR-4, which is an industry standard abbreviation for Flame Retardant 4. The LEDs and detectors come in industry standard packages which are attached to the PCB using methods well known in the art. Small wedges can be place in between the LEDs and the PCB in order to orient the LED at an angle that is not at 90% to the plane of the PCB. The module itself is either physically attached to the movement mechanism of the x-y or x-y-z stage, for example but not limited to the case of a scanning configuration. In the case of the super array, whereby modules are attached together, the flexibility is obtained by securing the modules to one another on a single plane, so as to allow for motion in response to changes in z.

Figure 5I:
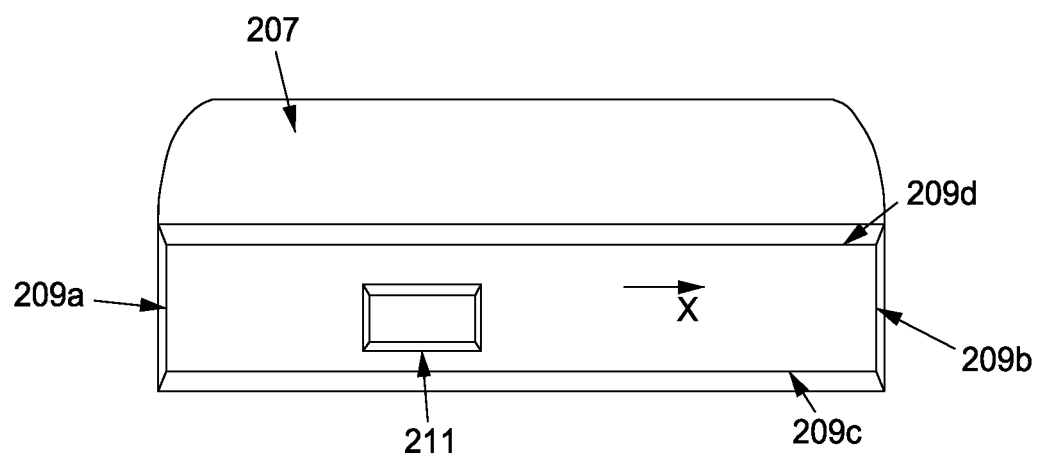
FIG. 5I shows an image of an airtight mattress and frame with a module in the mattress. The module is capable of movement on a x-y stage.
Figure 5J:
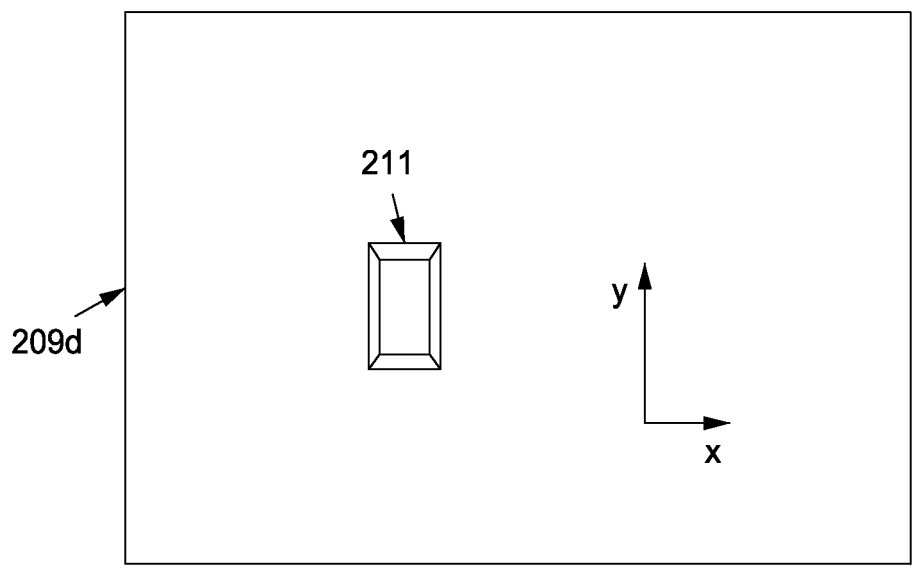
FIG. 5J is a top view of the image described in 5I.
Figure 5K:
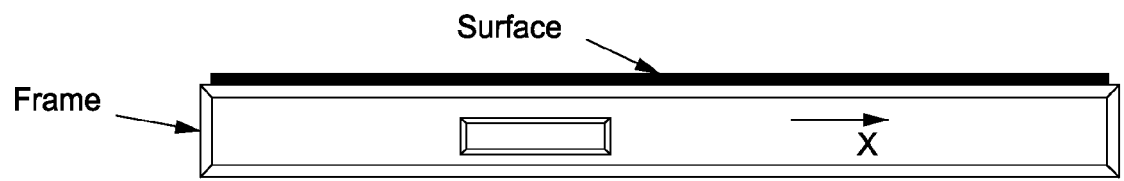
FIG. 5K shows an x-y stage frame with top attachable surface shown in horizontal orientation so that a person may lay atop the surface.
Figure 5L:
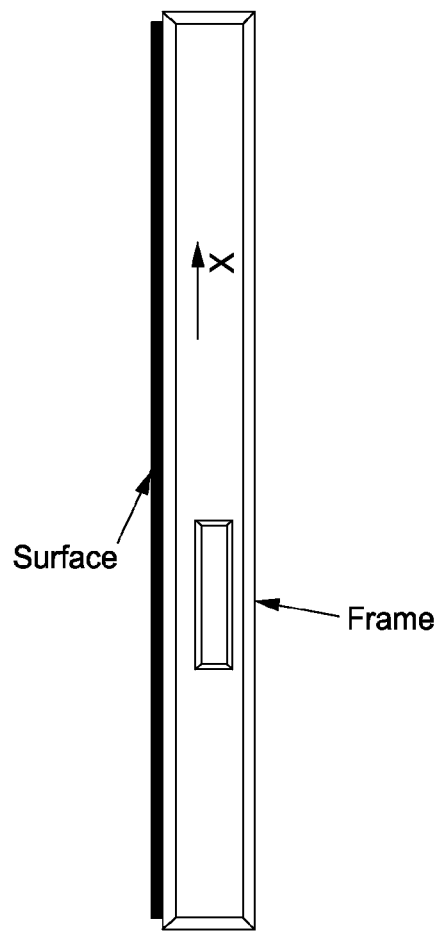
FIG. 5L shows the x-y stage frame with top attachable surface shown in vertical orientation so that a person may stand or otherwise be positioned adjacent to the surface in a vertical position.

FIG. 5I shows an image of an airtight mattress 207 and frame 209 with a module 211 in the mattress. The module 211 is capable of movement on a x-y stage. FIG. 5J is a top view of the image described in 5I, comprising a mattress 207, a frame 209 and a module 211. FIG. 5K shows an x-y stage frame with top attachable surface shown in horizontal orientation so that a person may lay atop the surface. The surface may be rigid (e.g. glass or plexiglass) or made of non-rigid materials (e.g. cloth or pliable plastic). FIG. 5L shows the x-y stage frame with top attachable surface shown in vertical orientation so that a person may stand or otherwise be positioned adjacent to the surface in a vertical position. The surface may be rigid (e.g. glass or plexiglass) or made of non-rigid materials (e.g. cloth or pliable plastic). The frame may be placed onto a support structure that may vary the orientation at any angle between vertical and horizontal, in this way varying the pressure applied to the person.

Figure 6A:
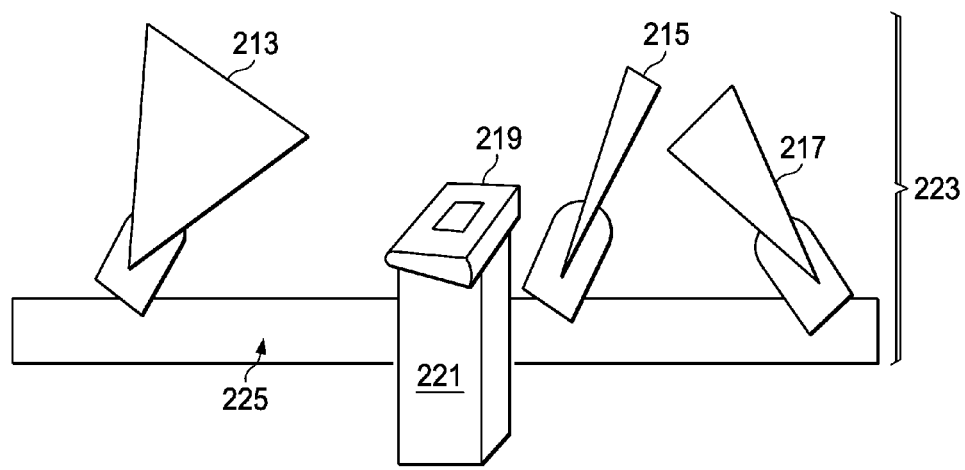
FIG. 6A shows different light/detector embodiments as part of a module. The light source is shown at different orientations, positions, and angles of emission.

FIG. 6A depicts different light/detector embodiments as part of a module 223. Three light sources 213, 215, and 217 are shown at different orientations, positions, and angles of emission. The detector 219 of module 223 is mounted on a solid support 221. The light sources 213, 215, and 217 and detector base 221 of module 223 are all mounted on a solid base 225.

Figure 6B:
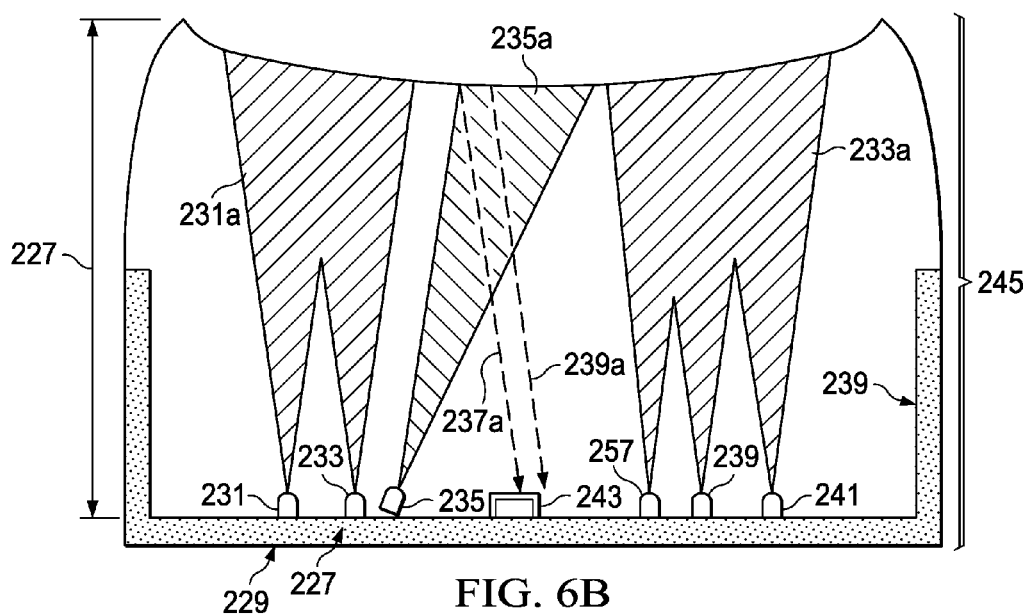
FIG. 6B shows a module embedded in a mattress with a changing angle of incidence as a function of the surface curvature. The figure further shows the benefit derived from multiple light sources to optimize transmission and minimize spectral reflectance onto imager.

FIG. 6B shows a module 245 embedded in a mattress 227. The module has a base 229 and six different light sources 231, 233, 235, 237, 239, and 241. The module 245 has a detector 243. 231a represents the light beam emitted from light sources 213 and 233. 235a represented the light beam emitted from light source 235. 233a represents light beam emitted by light sources 237, 239 and 241. 237a and 239a are the reflected light rays that fall on detector 243. The light sources emit light with a changing angle of incidence as a function of the surface curvature. FIG. 6B further shows the benefit derived from multiple light sources to optimize transmission and minimize specular reflectance onto the imager.

Figure 6C:
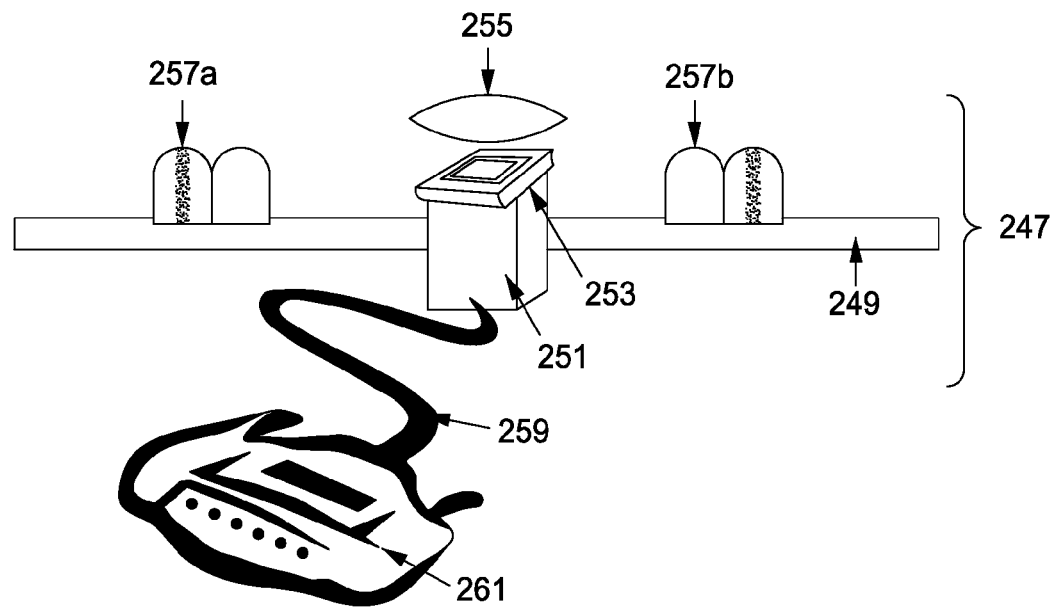
FIG. 6C shows different light/detector embodiments as part of module with a cable connector to an external processor.

FIG. 6C shows a module 247, comprising a base 249, two LEDs 257a and 257b, a detector 253, a lens 255 and a detector support 251 attached to the base 249. A cable connector 259 connects an external processor 261 to the module 247. The imager portion is shown to be within the box with an assembly that contains electrical connectors that are passed through to the outside connector. A filter can be added below the lens 255 in FIG. 6C and above the detector 253 to reduce the amount of background light that is incident upon the detector at wavelengths that are not of interest.

Figure 6D:
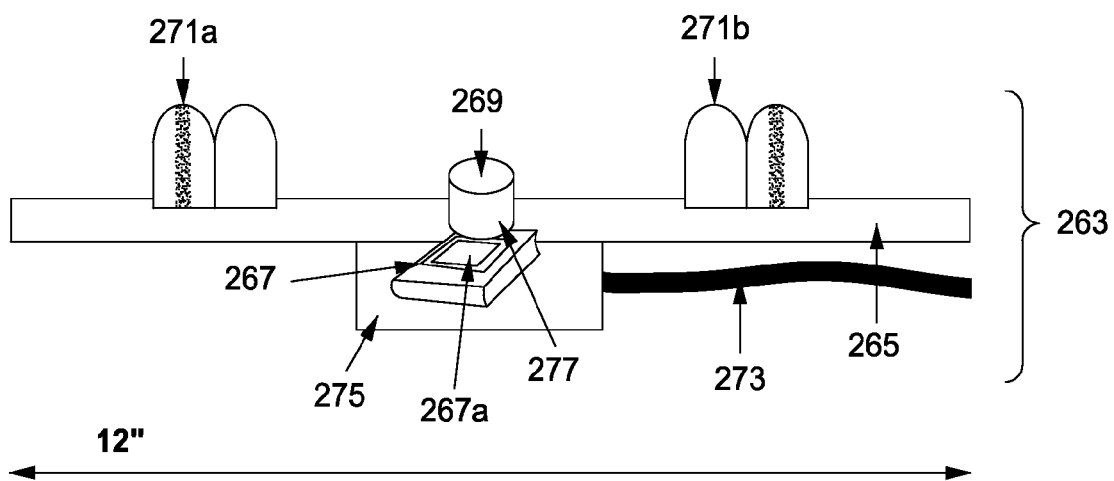
FIG. 6D shows different light/detector embodiments as part of module with a processor.

FIG. 6D shows different light/detector embodiments as part of module with a processor. Module 263 comprises of a base 265, a chip 267a, light sources 271a and 271b, detector 267 at the base of a solid structure 277. The module 263 is connected to an external processor 275 with a connection 273. The solid structure 277 has a lens 269 at the top. The optical lens assembly is shown to pass through the box with the electronics located below. FIG. 6D shows an additional chip 267a in the rectangular box below the module that was supposed to represent a signal processor capable of analyzing the data and controlling the system.

The lenses 255 and 269 are important because they allow for the collection of the light from the patient and the subsequent imaging of that light onto the plane of the underlying detector array. The specific lens type and properties are selected based upon the distance between the lens and the patient, as well as the area to be imaged. The lenses are also able to adjust the focus of the optical system.

The imaging detector arrays of the present invention are almost always rectangular or a square. In the figures, if a circle is shown it is meant to represent the lens that would normally cover the detector array chip. Often times the entire assembly of the lens, any filter, holder, and detector chip is referred to as an imager or imaging module.

There is an advantage in using imagers that allow for non-linear response curves in the present invention. That is to say, that the output of the device is not linearly proportional to the intensity of light incident upon it. The reason this is advantageous is that it has the affect effect of increasing the dynamic range of the system. In this way, slight changes in intensity in dark regions can still be resolved well even when the scene includes very bright regions. For example, very bright regions could be the result of background room lighting in non covered mattress areas or the result of specular reflections from wrinkles on the mattress surface. The two CMOS based imagers from Sensata and from Texas Instruments, both offer the capability of using non-linear response curves.

Figure 6E:
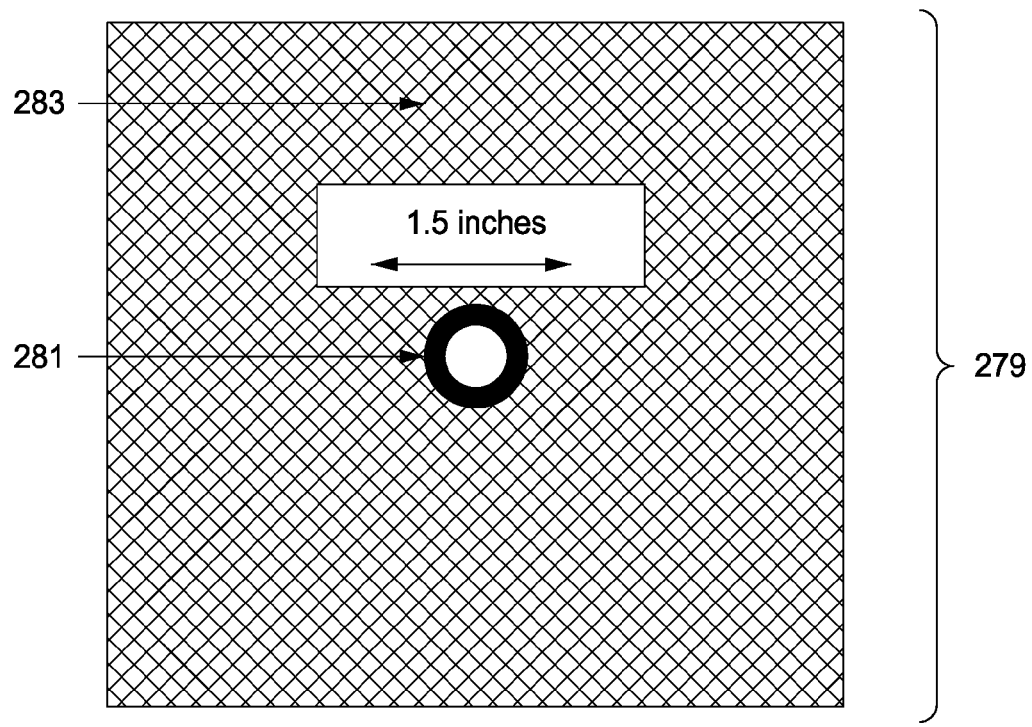
FIG. 6E is a top view of a module with hundreds of LEDs connected.

FIG. 6E is a top view of a module 279, having a detector 281. Module 279 has an array of LEDs 283 (with over a hundred LED units connected).

Figure 6F:
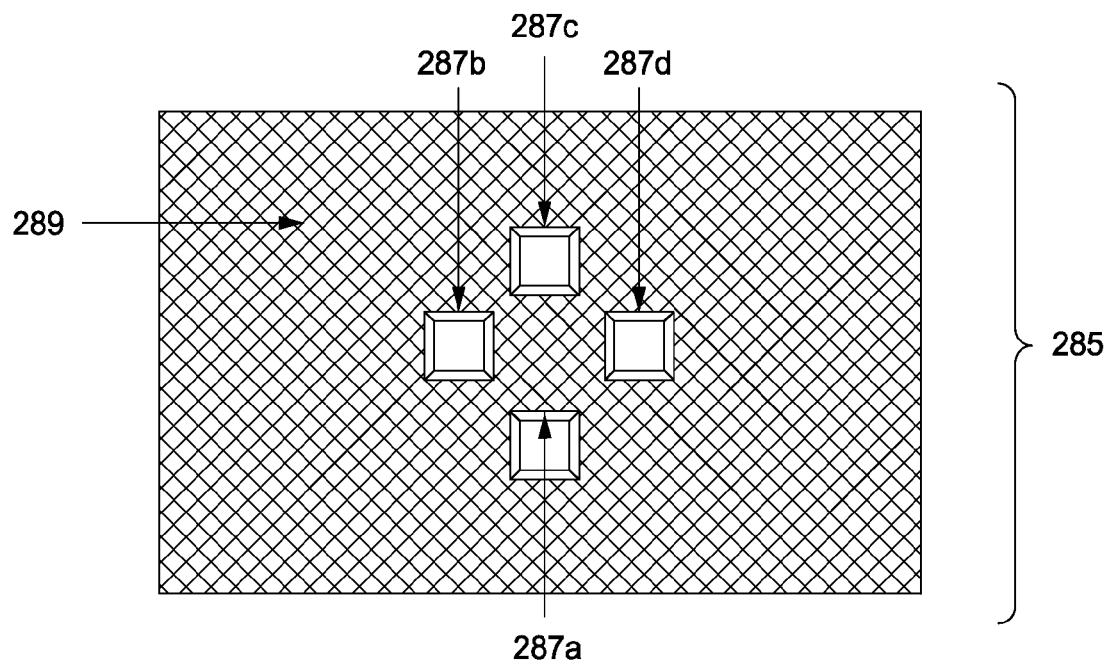
FIG. 6F is a top view of a module with hundreds of LEDs and multiple detectors.

FIG. 6F is a top view of a module 285 with four detectors 287a, 287b, 287c, and 287d. Module 285 has an array of LEDs 289 (with over a hundred LED units connected).

Figure 6G:
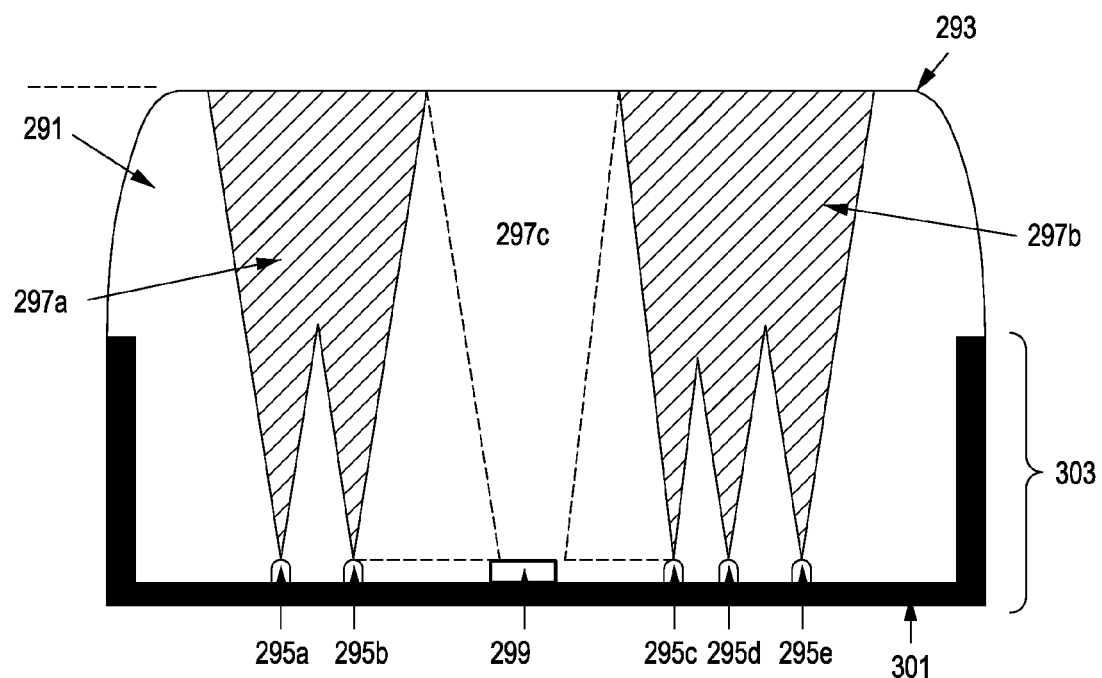
FIG. 6G is an image of a module embedded in an airtight mattress with a transparent plastic cover, and having multiple light sources to optimize transmission and minimize spectral reflectance onto imager.

FIG. 6G is an image of a module 303 embedded in an airtight mattress 291 with a transparent plastic cover 293, and having multiple light sources 295a, 295b, 295c, 295d, and 295e to optimize transmission and minimize spectral reflectance onto imager 299. The module 303 has a base 301, to which the light sources 295a-295e and the imager 299 are attached. Light sources 295a and 295b emit a beam of light 297a, light sources 295c-295e, emit a beam 297b. Light reflected back to the imager 299 is shown by 297c.

Figure 6H:
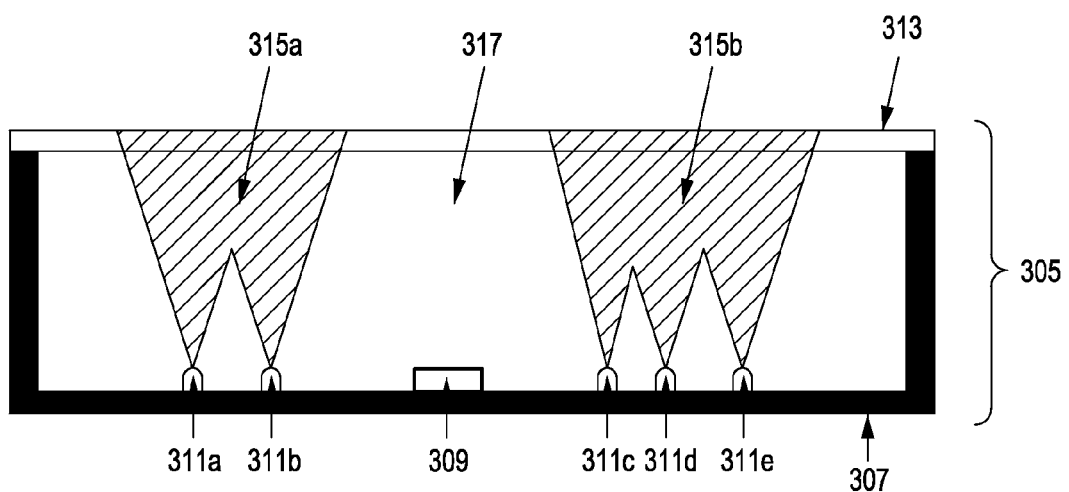
FIG. 6H is an image of a module embedded in a mattress with a transparent plastic or glass cover, and having multiple light sources to optimize transmission and minimize spectral reflectance onto imager.

FIG. 6H is an image of a module 305 embedded in a mattress 317 with a transparent plastic or glass cover 313, and having multiple light sources 311a-311e to optimize transmission and minimize spectral reflectance onto imager 309. Light sources 311a and 311b emit a beam of light 315a, light sources 311c-311e, emit a beam of light 315b.

Figure 6I:
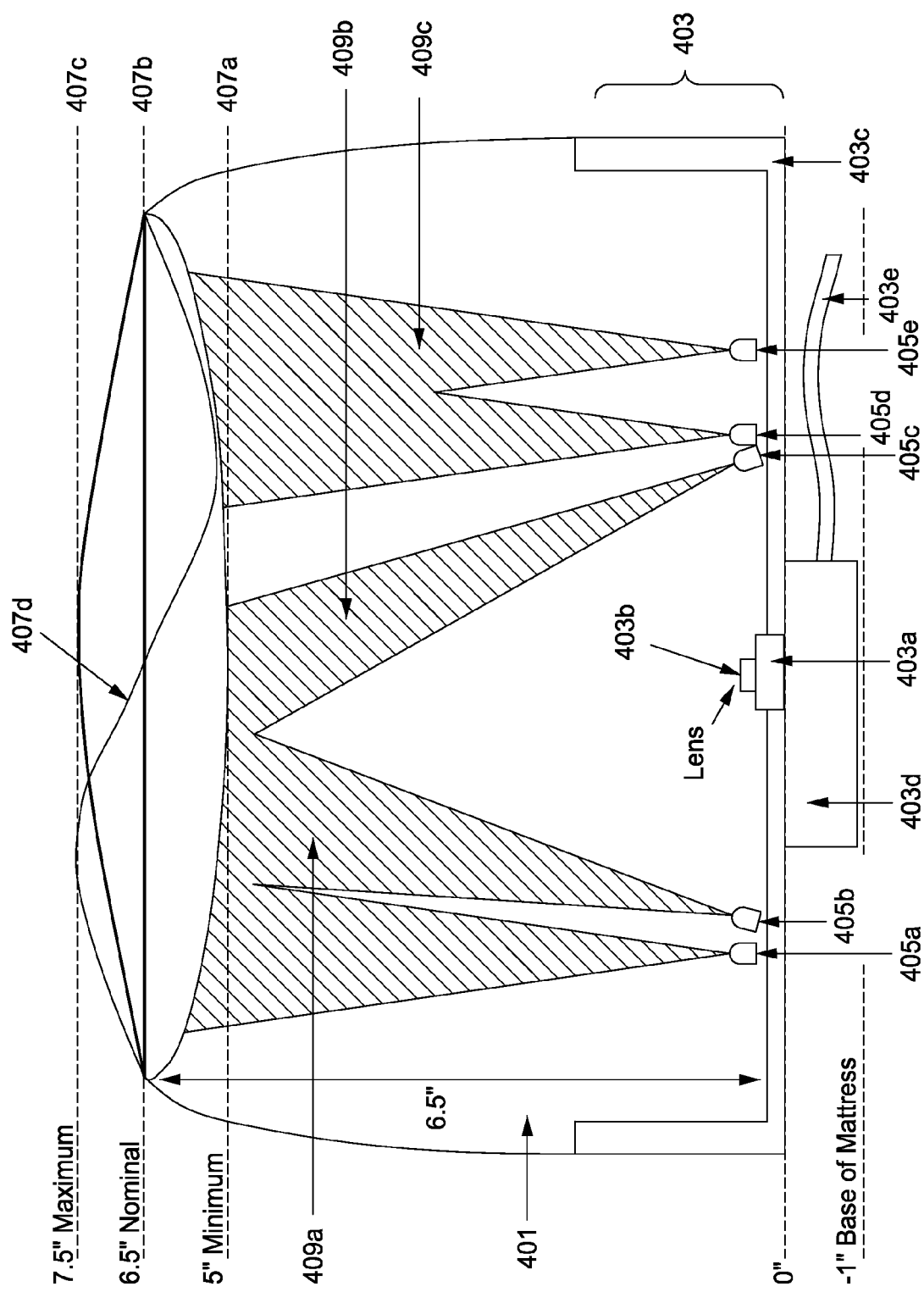
FIG. 6I is an image of a module embedded in a mattress with a transparent plastic cover (window), and having multiple light sources to optimize transmission and minimize spectral reflectance onto imager. The figure is a side view which shows three positions of the top plastic window.

FIG. 6I is a side view of a module 403 embedded in a mattress 401. Module 403 has a detector 403a, a lens 403b, a base 403c, a solid structure 403d located 1" below the base of mattress 401, and a connection 403e, located below the base of mattress 401. The mattress has a transparent plastic cover (window) 407b and multiple light sources 405a, 405b, 405c, 405d, and 405e optimize transmission and minimize spectral reflectance onto detector 403a. Light sources 405a and 405b emit a beam of light 409a, light source 405c emits light beam 409b, and light sources 405d-405e, emit a beam 409c. The plastic window 407b can change shape and position relative to the base of mattress 401, to account for under inflation, over inflation or non-uniform pressure exhibited by the patient over the imaging area. The design should consider these factors and identify ways to provide sufficient illumination to the patient under the variety of conditions. To further constrain the problem, the mattress window height above the imager should be allowed to vary between 5" (407a)-7.5" (407c) with 6.5" (407b) chosen as the nominal flat in cases where the mattress is intended to replace a hospital mattress, so that typical side rail heights will still provide adequate safety for a patient. The first modeled window position is with the mattress 401 flat at 6.5" (407b). Both a concave (407a) and convex (407c) window format should be used as the $2^{nd}$ and $3^{rd}$ window positions to be modeled, with the center point at the corresponding limit and the end points at the nominal position. The $4^{th}$ window position shall correspond to an asymmetric orientation (407d).

In cases where the mattress bends appreciably or creases form, certain LED placements can lead to direct specular reflections from the top surface of the mattress back onto the detector. The system solution for this problem is to determine which LEDs are causing specular reflections and turn those off. Hence the design allows for a sufficient number of LEDs with placements such that particular LEDs that are causing specular reflections may be turned off, while the others of the set of LEDs are still capable of illuminating the entire surface area. This means that LEDs must be positioned such that specific surface regions will be illuminated by multiple LEDs from multiple angles. 256 LEDs of each wavelength may be placed, however designs that require far fewer LEDs would yield significant value in terms of ultimate product cost and PCB board layout. It is desirable to use fewer LEDs as much as possible.

The present invention is not limited to applications within healthcare, nor to the use of wavelengths that are selective to oxygenated or deoxygenated hemoglobin, but rather can be applied generally to distinguish between arbitrary targets and non-targets provided that such have differing frequency behaviors in magnitudes, phase or both of the time variations within the captured spatial images for the particular illumination wavelengths and conditions. As a further example, the invention may be used for the detection of items that have little or no time variation of their optical properties in the case where these items are placed in between the imager and an object having a time variation of its optical properties, with the latter providing the contrast needed to identify and inspect the former. Such may be the case for a security application where the present invention is utilized to identify inanimate objects that are hidden underneath clothing.

Figure 7A:
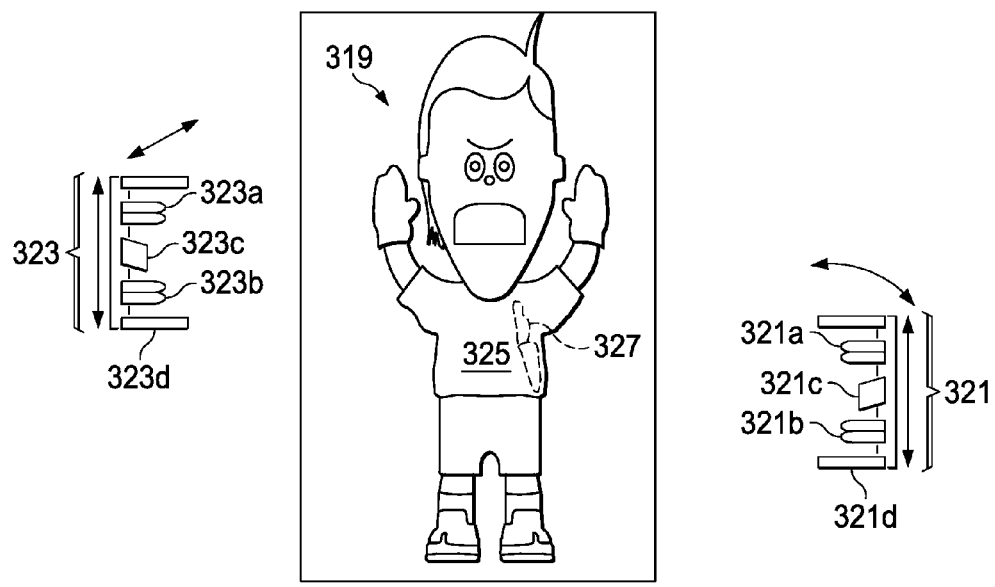
FIG. 7A is an image of an airport scanner/detector having single modules capable of being orientated on a x-y translation stage and curved translation stage for detection of subjects carrying concealed body weapons.

FIG. 7A is an image of an airport scanner/detector 319 having two single modules 321 and 323 capable of being orientated on a x-y translation stage and curved translation stage for detection of a subject 325 carrying a concealed body weapon 327. The module 321 has a base 321d, two light sources 321a and 321b and a detector 321c. The module 323 has a base 323d, two light sources 323a and 323b and a detector 323c.

Figure 7B:
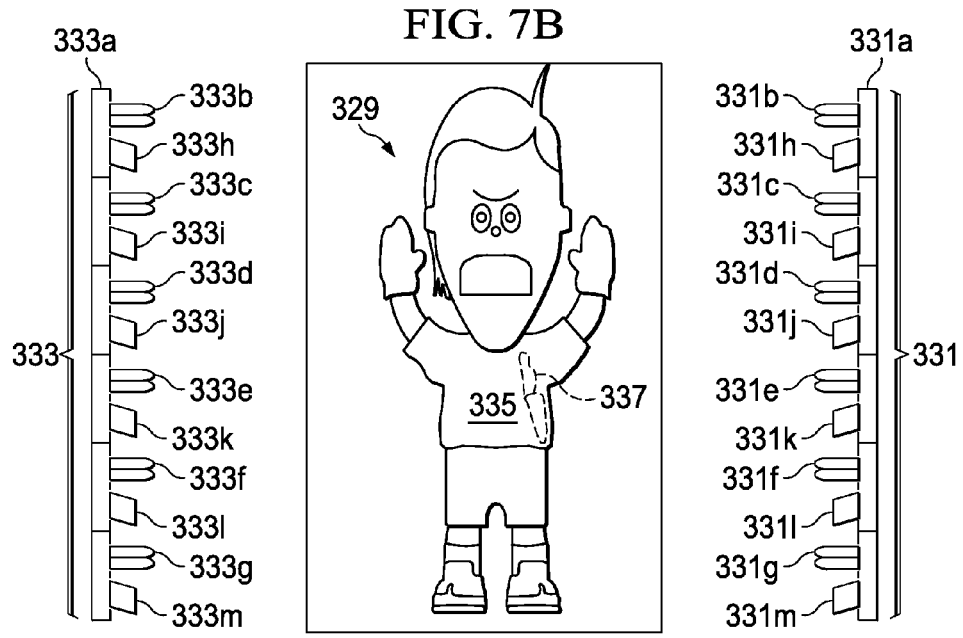
FIG. 7B is an image of an airport scanner/detector having strips of modules (light sources and detectors) for detection of subjects carrying concealed body weapons.

FIG. 7B is an image of an airport scanner/detector 329 having two strips of modules 331 and 333 (light sources and detectors) for detection of a subject 335 carrying a concealed body weapon 337. Module strip 331 has a base 331a, light sources 331b-331g and detectors 331h-331m. Module strip 333 has a base 333a, light sources 333b-333g and detectors 333h-333m.

In order to record the time variations of the captured spatial images at time scales fast enough to observe dynamic behaviors that result from the beating heart or pulsatile blood flow it is necessary to record many samples each second for the various wavelengths and lighting conditions. As such it is necessary to provide electronics that allow for the rapid control of the lighting conditions. As an example, for the case where two wavelengths are desired and the illumination properties may be achieved by using LEDs, a simple circuit may be constructed to provide for driving of multiple LEDs of each type whereby the particular wavelength of LEDs that is turned on is determined by the sign of the power supply and whereby the background condition may be affected when the power supply bias is zero.

Figure 8:
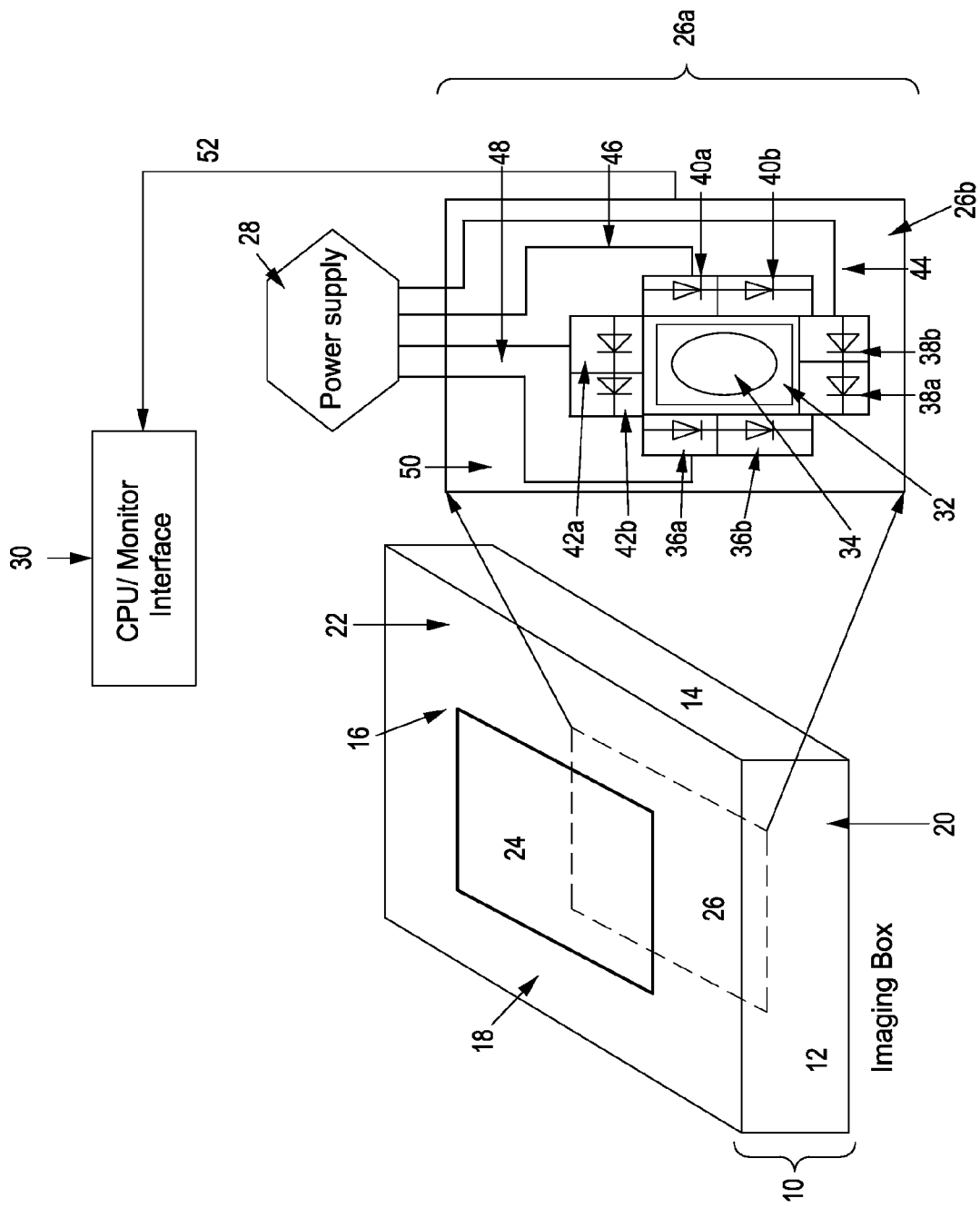
FIG. 8 is a representation of a LED circuit diagram. The circuit arrangement depicted in the figure provides for an alternating background (LEDs off), LED1 (for e.g. 660 nm) and LED2 (for e.g., 890 nm).

A LED circuit diagram is shown in FIG. 8. The circuit arrangement provides for an alternating background (LEDs off), LED1 (for e.g. 660 nm) and LED2 (for e.g., 890 nm). The circuit diagram has an imaging box 10, having a base 20, a top portion 24, and four sides 12, 14, 16 and 18. An imager array 26 is mounted on the top portion 24. The imager array 26 is made up of one or more imaging cells 26a. The imaging cell 26a, comprises an imaging chip 32 containing a lens 34. Eight light sources or LEDs 36a, 36b, 38a, 38b, 40a, 40b, 42a, and 42b are present around the imaging chip 32. The LEDs, 36a, 36b, 38a, 38b, 40a, 40b, 42a, and 42b and the imaging chip 32 are mounted on a PCB 26b, that provides mechanical support. LEDs 36a and 36b are connected to a power supply 28 by an electrical connection 50. LEDs 38a and 38b are connected to a power supply 28 by an electrical connection 44. LEDs 40a and 40b are connected to a power supply 28 by an electrical connection 46. LEDs 42a and 42b are connected to a power supply 28 by an electrical connection 48. The digital signal from the imaging cell 26a is relayed to a PC 30 via a standard connection 52.

Figure 9A:
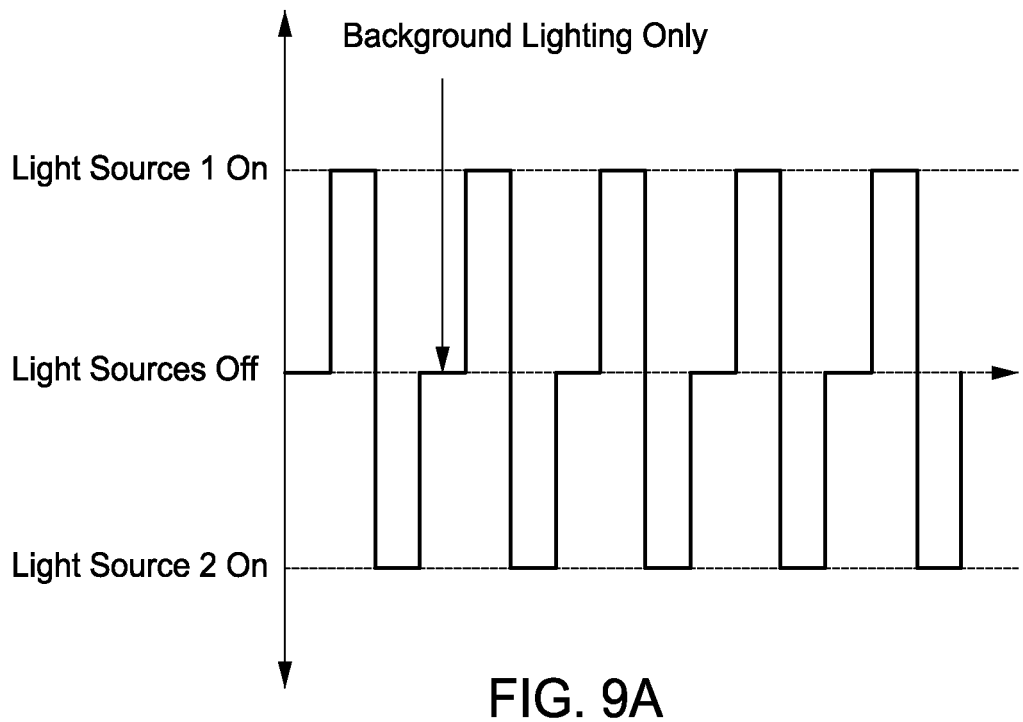
FIG. 9A shows a sample LED driving bias that provides for an alternating background (LEDs off), a light source 1 (for e.g. 660 nm), and a light source 2 (e.g. 890 nm).
Figure 9B:
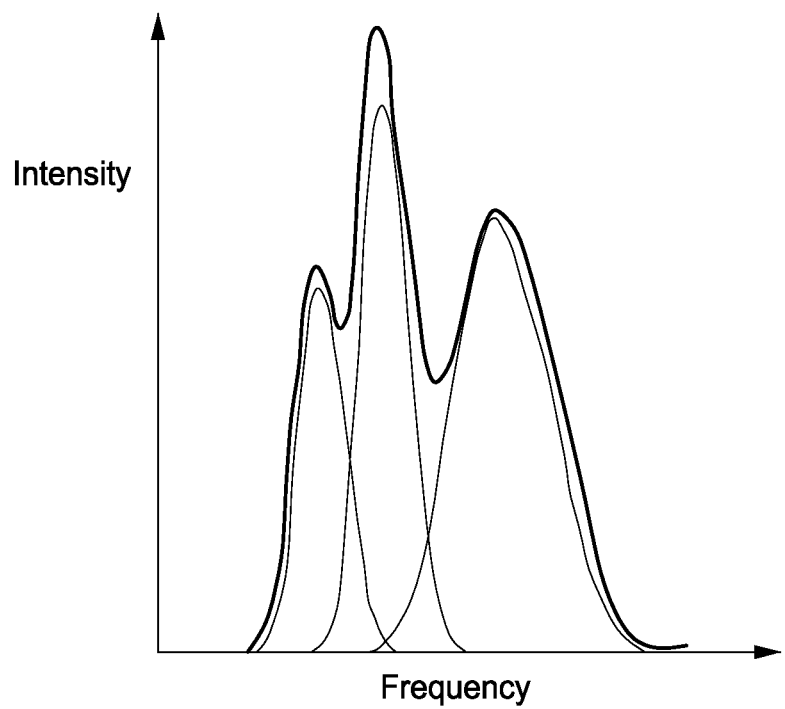
FIG. 9B shows a complex emission spectra of a possible light source 1 comprised of a combination of individual LEDs of varying intensity, center frequency and FWHM.
Figure 9C:
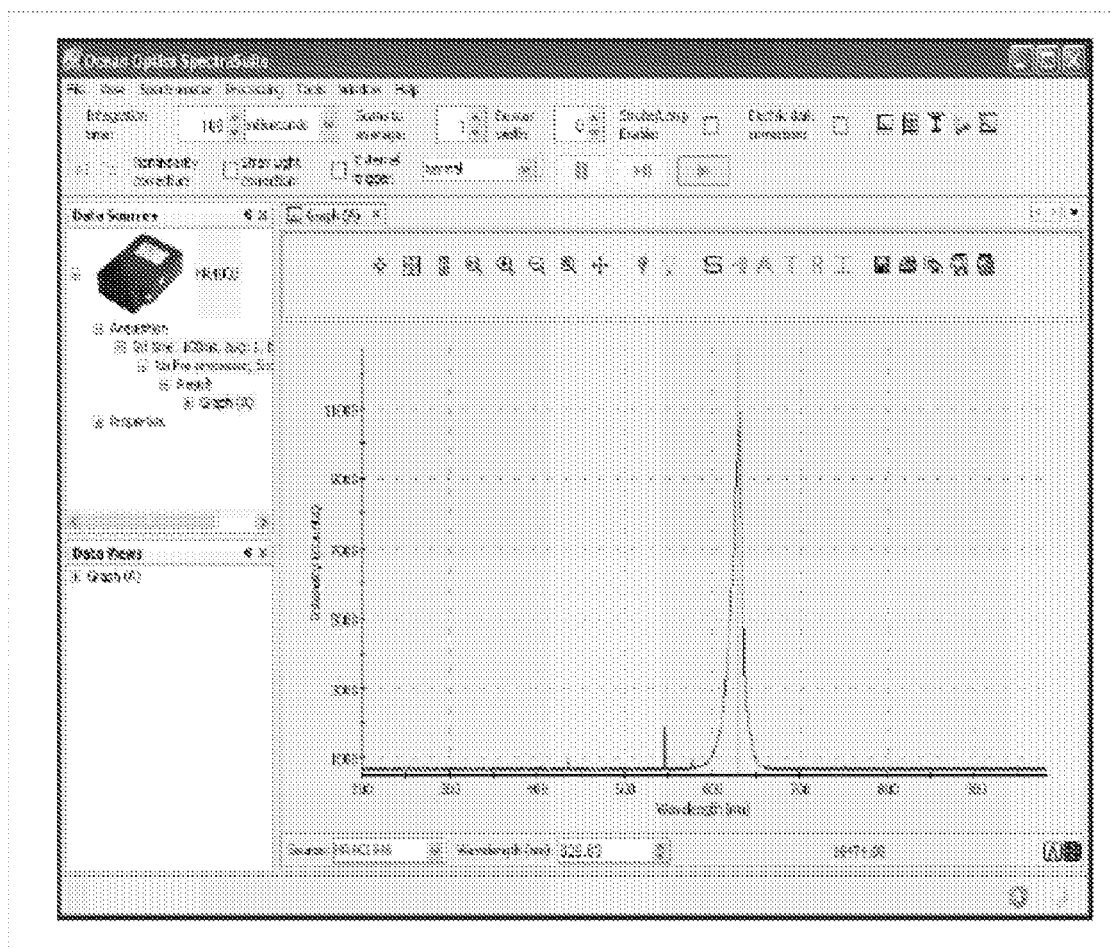
FIG. 9C is a screen shot of the Ocean Optics SpectraSuite® Software Sample Emission Spectra of a Red LED centered at 630 nm with FWHM of approximately 15 nm.

Furthermore, it is important that each lighting condition follow in quick succession so as to minimize errors associated with phase variations. As such a repetitive sequencing between the various illumination conditions may be achieved by a repetitive cycling through the different bias conditions (as shown in FIG. 9A). It may be the case that arbitrary illumination distributions over a set of wavelengths is desirable instead of the substantially monochromatic illumination provided by a typical LED. In such cases, LEDs of varying wavelengths and intensities may be combined to form arbitrary distributions (as shown in FIG. 9B). Appropriate electronic circuits to control such a combination of LEDs for a specific light condition may included parallel combinations of LEDs with power supply dividers that enable differing intensity levels for each LED. Other electronic circuits are possible as is well known in the art. A typical illumination spectral distribution is shown in FIG. 9C for an LED having a peak wavelength of approximately 630 nm and a full width at half maximum of approximately 10 nm. Wavelengths of arbitrary peak positions and varying full width at half maximums are obtainable using semiconductor fabrication methodologies that are well known in the art.

Figure 10A:
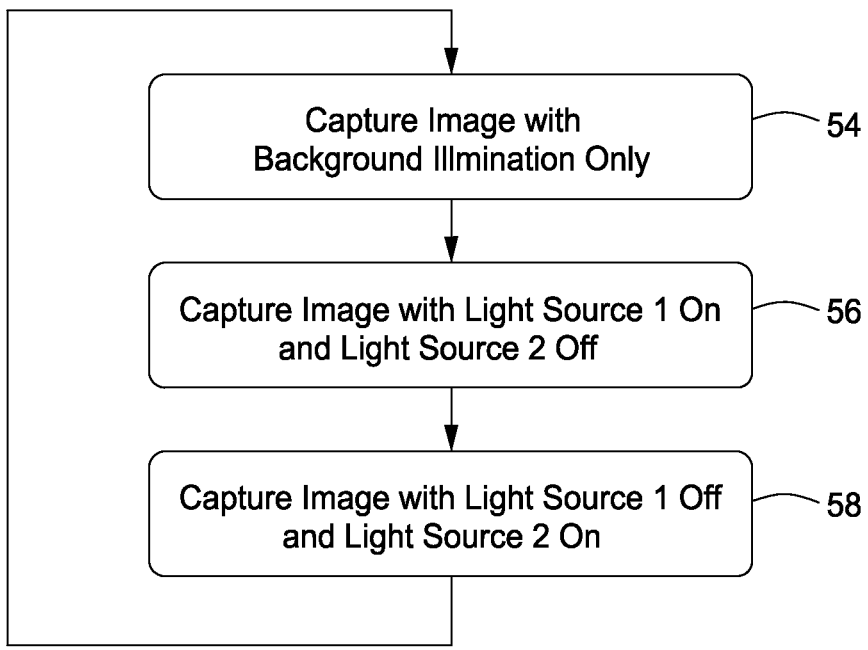
FIG. 10A is a block diagram summarizing a typical illumination timing scheme cycle.

A block diagram summarizing a typical illumination cycle is shown represented in FIG. 10A. The illumination cycle starts at step 54 where an image is captured with only a background illumination, during which the LEDs are turned off. Step 54 is followed by step 56, wherein light source 1 (for e.g. 660 nm) is turned on and light source 2 (for e.g. 890 nm) is turned off and the image is captured. Step 56 is followed by image capture step 58, during which light source 2 (890 nm) is turned on and light source 1 (660 nm) is turned off. Step 54 is then repeated after step 58, completing the cycle.

Figure 10B:
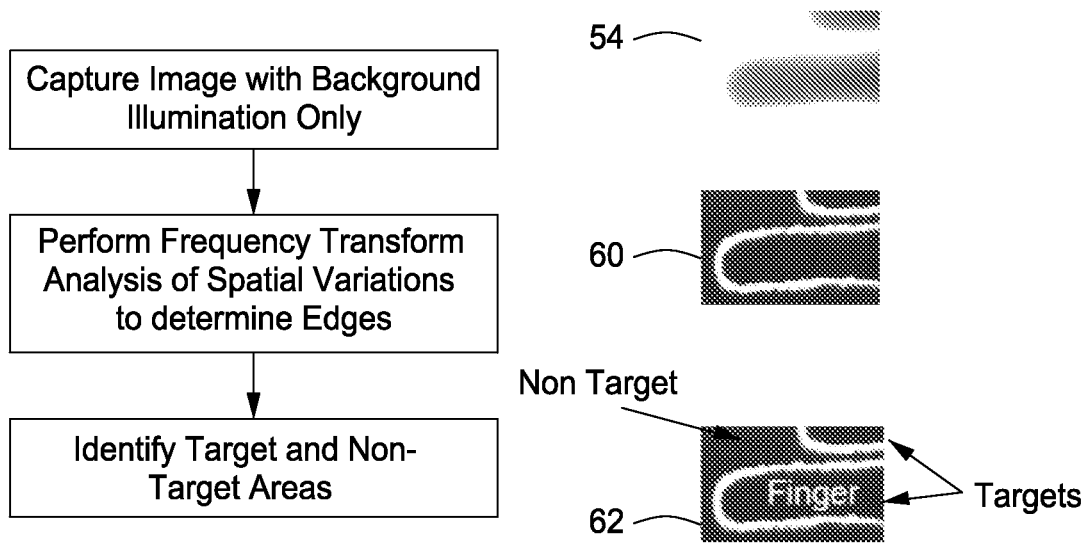
FIG. 10B shows a scheme for performing a spatial transform analysis for determining areas of interest.

A scheme for performing a spatial transform analysis for determining areas of interest in a target (finger) or non-target (air) is shown in FIG. 10B. Spatial transform analysis begins with step 54, where an image is captured with only a background illumination, during which the LEDs are turned off. Step 54 is followed by step 60 wherein a frequency transform analysis of the spatial variations (Fourier or Hough) is performed to determine the edges. Finally in step 62, target (fingers) and non-target (air) is identified based on the results of step 60.

Figure 10C:
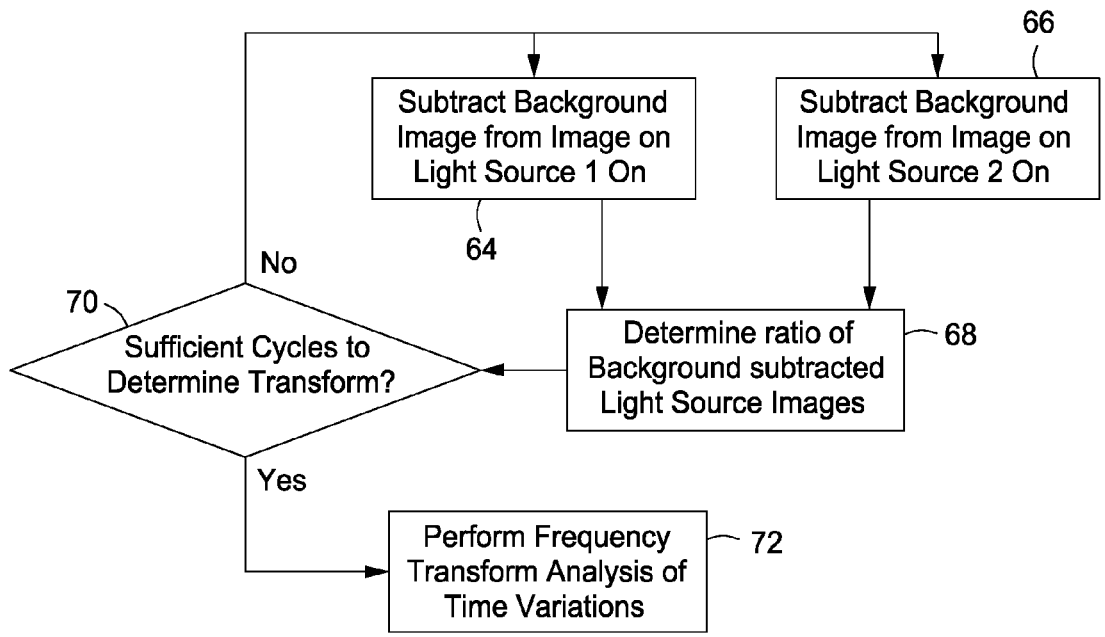
FIG. 10C shows a scheme for background correction and determination of ratio for each timing cycle.

The scheme for background correction and determination of ratio for each timing cycle is shown in FIG. 10C. Steps 64 and 66 involve subtraction of background images from images obtained with light sources 1 and 2 switched on, respectively. After steps 64 and 66 are completed, the ratio of background subtracted light images is determined in step 68. The completion of step 68 initiates a feedback mechanism (step 70) to determine if the cycle number is sufficient to proceed to step 72. If yes, step 72, is performed wherein a frequency transform analysis of time variations is done. If the cycle number as determined by step 70 is insufficient, then steps 64, 66, and 68 are repeated till the time there are sufficient number of cycles to proceed to step 72. It is also possible to conduct an analysis of the frequency behavior of the time variations for each of the lighting conditions independently.

Figure 10D:
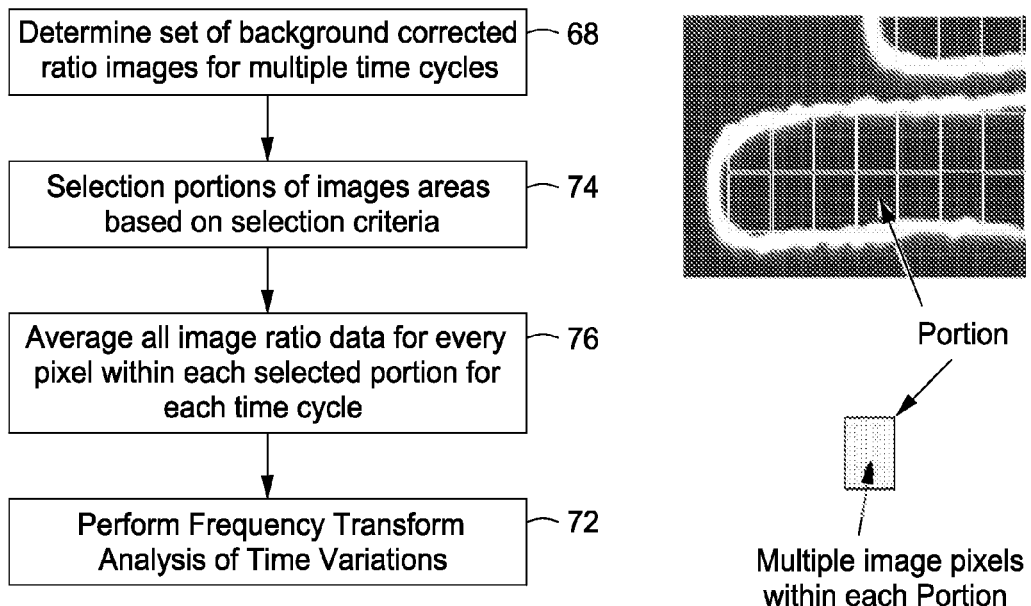
FIG. 10D shows a scheme for performing gross frequency transform analysis of the time variations to identify "hot regions".

FIG. 10D represents a scheme for performing gross frequency transform analysis of the time variations to identify "hot regions". The process begins with 68 wherein ratio of background subtracted light images for the multiple cycles is determined. After the completion of step 68, a portion of the target (finger) image areas are selected based on a selection criteria (step 74). This is followed by step 76, wherein image ratio data is averaged for every pixel within each selected portion for each cycle. Finally, step 72 is performed wherein a frequency transform analysis of time variations is done.

Figure 10E:
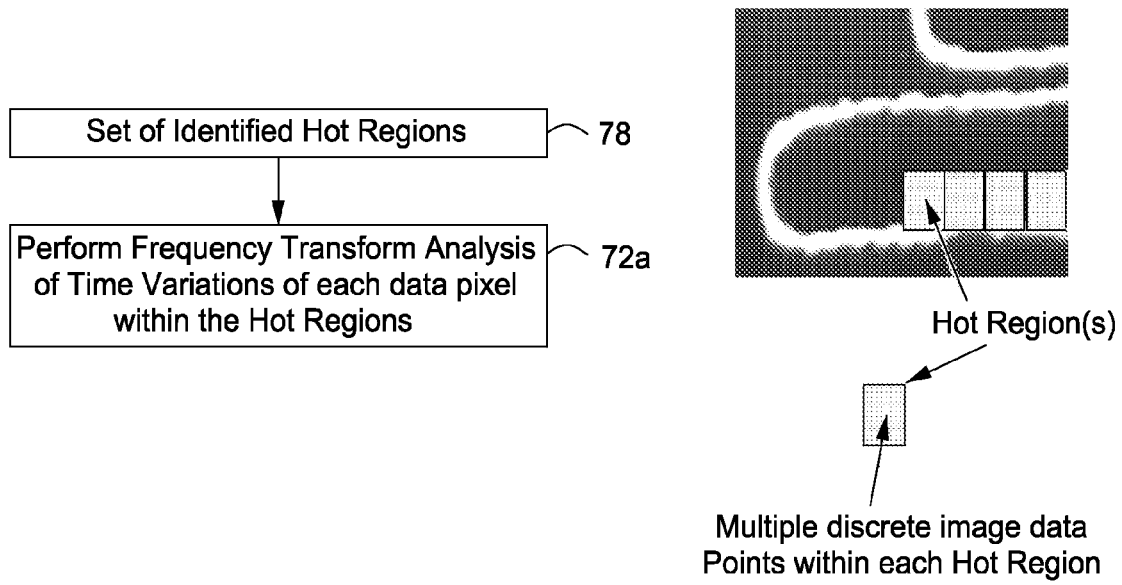
FIG. 10E shows a scheme for performing a refined frequency analysis to detail flow parameters in areas within "hot regions".

A scheme for performing a refined frequency analysis to detail flow parameters in areas within "hot regions" is depicted in FIG. 10E. A set of identified "hot regions" is identified with the target (finger). This is done in step 78. After identification of the hot regions, 78, a frequency transform analysis of time variations (e.g. Fourier) of each data pixel within the selected "hot regions" is done (step 72a).

Figure 10F:
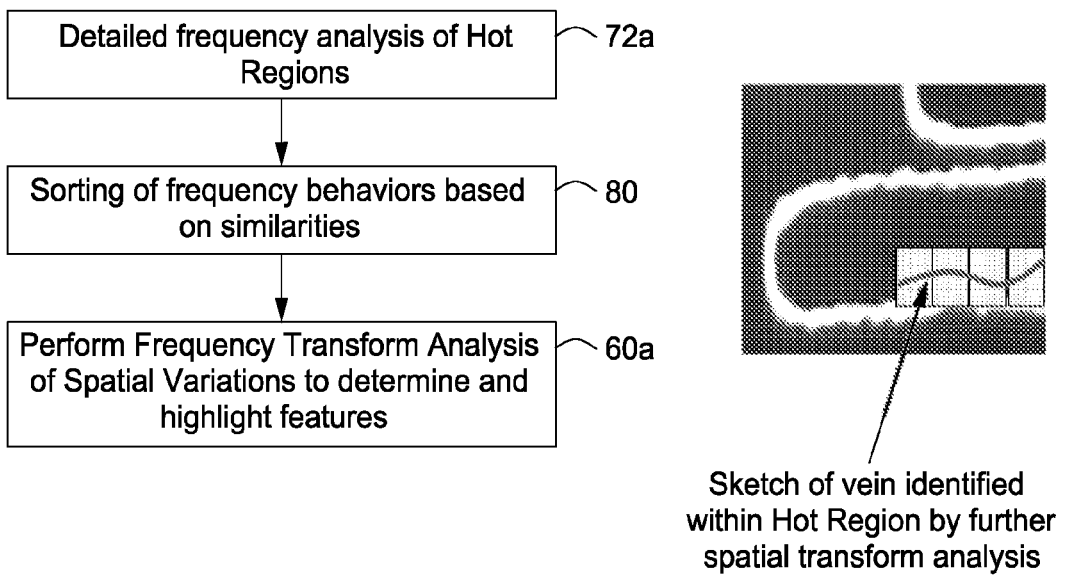
FIG. 10F shows an additional spatial transform analysis technique of detailed refined frequency analysis within "hot regions" to determine areas or features of similar frequency behavior.

In FIG. 10F an additional spatial transform analysis technique of detailed refined frequency analysis within "hot regions" to determine areas or features of similar frequency behavior is shown. The technique begins with a frequency transform analysis of time variations (e.g. Fourier) in the "hot regions" (step 72a). Step 72a is followed by step 80, where frequency analysis results are sorted based on similarities. Finally, a variation of the previously described step 60 is performed wherein, a frequency transform analysis of the spatial variations (e.g. Hough) is performed to determine the highlight features (step 60a).

Figure 11A:
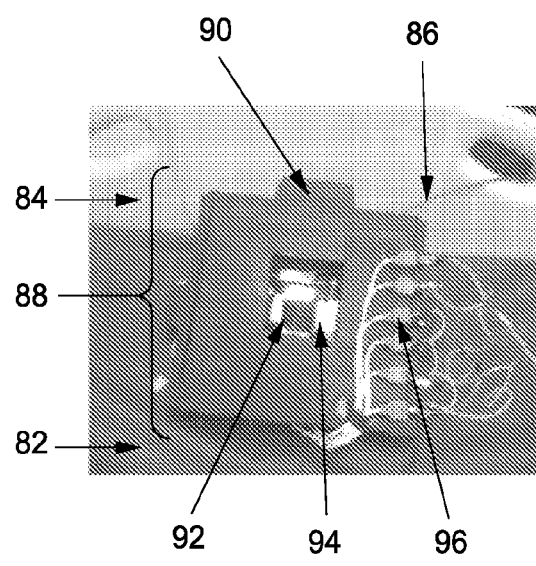
FIG. 11A depicts a prototype module shown with Red LEDs switched on (660 nm), in an absorbing box enclosure and wired interconnects.

FIG. 11A shows a prototype of an imaging module 88. Module 88 is placed on a mattress 82. The mattress 82 is supported by bed frame 84. The imaging module 88 is enclosed in a hard shell 90, has an imaging chip 92, red LEDs (660 nm) 94, and wired interconnects 96. The module can be connected to any monitoring/recording device or is accessible to the nurses/physician by an access point 86.

Figure 11B:
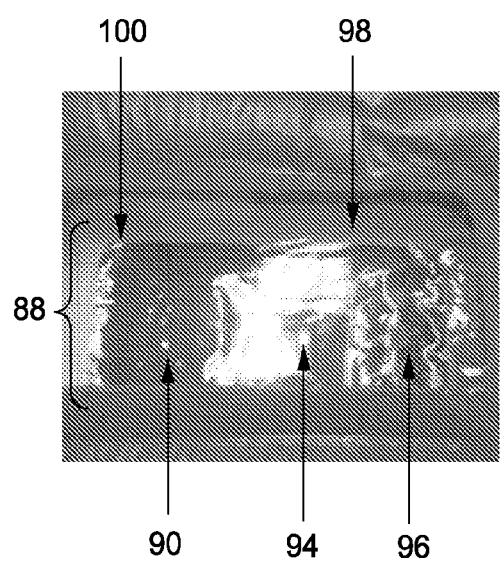
FIG. 11B shows the prototype module of FIG. 11A through a transparent air mattress with Red LEDs switched on (660 nm).

FIG. 11B depicts the imaging module 88 of FIG. 11A, embedded in a transparent air mattress 100, and having a transparent plastic case, 98 at the top. The imaging module 88 is enclosed in a hard shell 90, has an imaging chip 92, red LEDs (660 nm) 94, and wired interconnects 96.

Figure 11C:
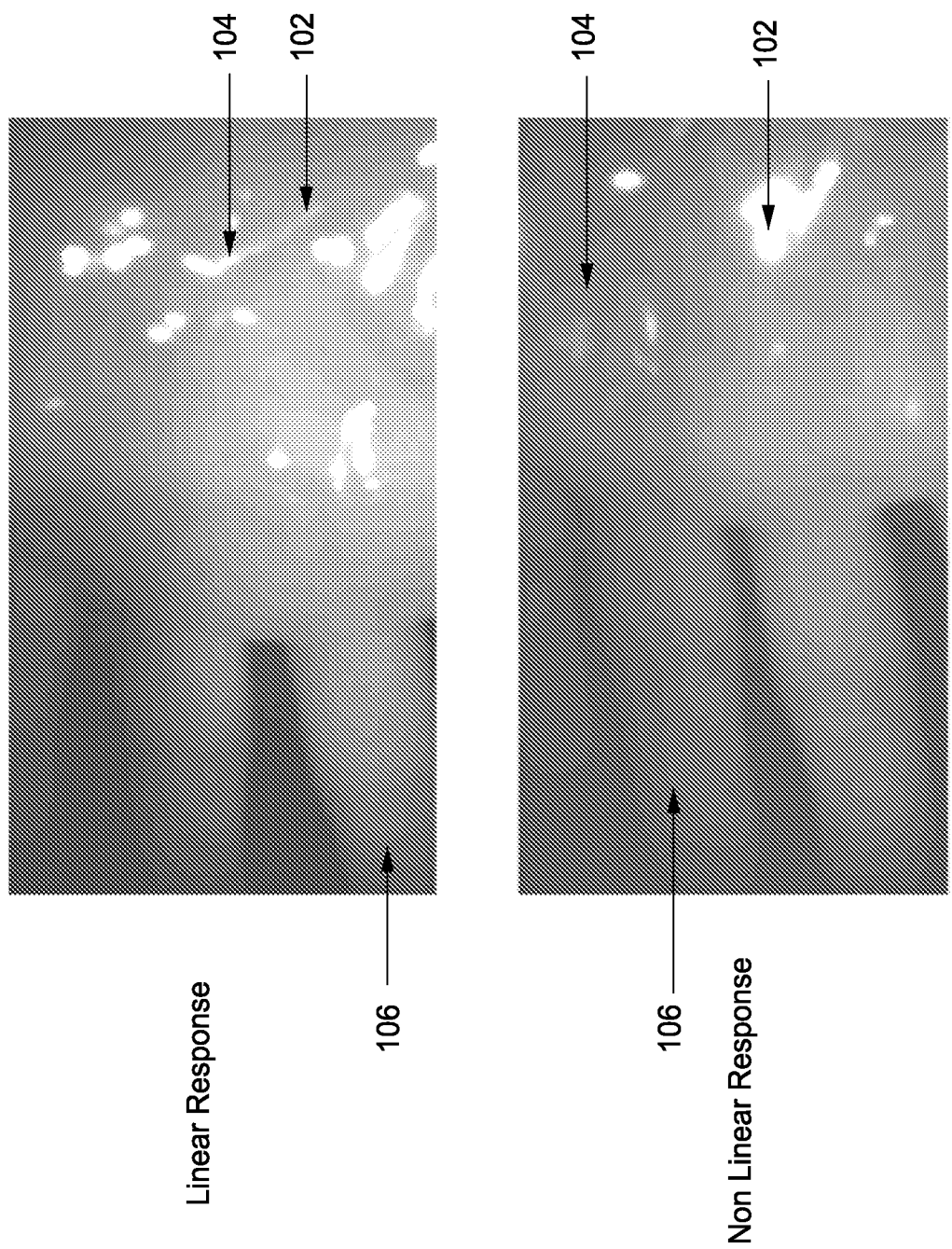
FIG. 11C shows the reduction of impact of specular reflection from a mattress surface through the use of non-linear detector response.

FIG. 11C shows a linear and a non-linear response obtained for a target (palm 104 and fingers 106) placed on a transparent plastic sheet or surface 102. Imaging through a window gives rise to specular reflections where a portion of light from the source bounces from the window onto the detector, without going through the window and interacting with the patient. As discussed previously in the present invention, the first approach is to design the position and orientation of light sources selected to reduce or eliminate specular reflectance. The problem is further exacerbated when the window is a deformable plastic mattress surface, in which case the optimum positions and orientations of the light sources may be different for different deformations of the mattress. The present invention, solves the problem by considering the range of common deformations and selecting a superset of LED numbers, positions and orientations. Then during operation of the system, LEDs that cause significant specular reflections for a particular state of window are identified (as they tend to work to saturate the detectors) and turned off. The remaining LEDs continue to provide illumination of the desired area, but without producing significant specular reflections. With that said, in cases where creases form in the mattress it may not be possible to completely eliminate the specular reflections from these regions without significantly impacting the illumination of nearby regions. It is not expected that these types of reflections can be avoided by the position and orientation of the light sources. FIG. 11C depicts two images where creases in the mattress surface cause specular reflections indicated by the variety of bright spots. FIG. 11C (top) depicts the image as viewed by a CMOS imager where the output is proportional to the intensity of the detected light. FIG. 11C (bottom) depicts a similar image viewed by a CMOS imager where the output is not proportional to the intensity of light. Such a non-linear response serves to limit the areas around the creases that result in saturation of the detector as can be seen by the future number of specular reflection points in the image. This aspect is particularly important for integrated bed imaging to work, wherein there will be conditions where the dynamic range of the light in the scene is simply to large to be adequately imaged by an imager operating in a linear mode.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims. An example would include the use of a wide variety of optical configurations or components such as mirrors, lenses, fiber optics, filters, choppers, semiconductor chips or materials which can be used individually or combined to create alternative optical geometries or advantages, but all of which serve to simply improve the illumination of the target scene and/or the collection of the image for analysis.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] Payette J R, Kohlenberg E, Leonardi L, Pabbies A, Kerr P, Liu K Z, Sowa M G, Assessment of Skin Flaps Using Optically Based Methods for Measuring Blood Flow and Oxygenation, Plast. Reconstr. Surg. 115:539-546, 2005.
[2] Payette J R, Kohlenberg E, Leonardi L, Pabbies A, Kerr P, Liu K Z, Sowa, M G, Laser Doppler & Optical Spectroscopy: Assessment of Skin Flaps Using Optically Based Methods for Measuring Blood Flow and Oxygenation, Plastic and Reconstructive Surgery, Volume 115(2), 539-546, 2005.
[3] Binzoni T, Vogel A, Gandjbakhche A H, Marchesini R, Detection limits of multi-spectral optical imaging under the skin surface, Phys. Med. Biol. 53, 617-636, 2008.
[4] Hauben D J, Baruchin A, Mahler A, On the history of the free skin graft, Ann Plast Surg., 9(3), 242-5, 1982.
[5] Bello Y M, Phillips T J, Recent advances in wound healing, JAMA, 283(6), 716-8, 2000.
[6] Leonardi L, Sowa M, Hewko M, Schattka B, Payette J, Hastings M, Posthumus T, Mantsch H H, Evaluating the Health of Compromised Tissues Using a Near Infrared Spectroscopic Imaging System in Clinical Settings: Lessons Learned, Proceedings of SPIE Vol. 4959, 89-99, 2003.
[7] Palero J A, de Bruijn H S, van der Ploeg-van den Heuvel A, Sterenborg HJCM, Gerritsen H C, In vivo nonlinear spectral imaging in mouse skin, OPTICS EXPRESS, Vol. 14, No. 10, 4395-4402, 2006
[8] Stamatas G N, Southall M, Kollias N, In Vivo Monitoring of Cutaneous Edema using Spectral Imaging in the Visible and Near Infrared, Journal of Investigative Dermatology (2006) 126, 1753-1760, 2006.
[9] Kerekesa J, Subramanian N, Kearney K, Schad N, Spectral imaging of skin: experimental observations and analyses, Medical Imaging 2006: Physics of Medical Imaging, Proceedings of SPIE Vol. 6142, 61423V, 2006.
[10] Mansfiled, J R, Sowa M G, Payette J R, Abdulrauf B, Stranc M F, Mantsch H H, Tissue Viability by Multispectral Near Infrared Imaging: A Fuzzy C-Means Clustering Analysis, IEEE TRANSACTIONS ON MEDICAL IMAGING, VOL. 17, NO. 6, 1011-1018, DECEMBER 1998.

What is claimed is:

1. An apparatus for noninvasive evaluation of a target versus a non-target, comprising:
   one or more light sources having at least one emission spectra directed at less than the entire target wherein the one or more light sources are configured to not contact the target;

two or more detectors positioned to capture light reflected from the target into two or more spatial images of the target at two or more times without contacting the target; and a processor for receiving the two or more spatial images, wherein the one or more light sources are positioned to minimize near-surface reflectance incident on the detectors, and wherein the processor further performs a transform analysis of time variations of at least a portion of the spatial images to distinguish between target and non-target image information.

2. The apparatus of claim 1, wherein the processor further measures the presence of one or more factors that lead to changes in tissue health selected from decubitus ulcers, cancerous lesions, skin transfers, skin temperature, skin oxygenation, burns, skin trauma, skin diseases, autoinflammatory diseases, autoimmune diseases, infectious diseases, and combinations thereof.

3. The apparatus of claim 1, further comprising an absorbing enclosure having raised sides to allow light reflected from the target to reach the one or more detectors to reduce or eliminate specular and near-surface reflectance incident on the detectors.

4. An apparatus for noninvasive evaluation of a target versus a non-target, comprising:
   one more light sources having a defined emission spectra and angle of illumination that illuminate a portion of the target not including a given image point on the target wherein the one or more light sources are configured to not contact the target;
   three or more detectors positioned to capture a target reflection comprising one or more two dimensional spatial images of the target without contacting the target; and
   a processor in communication with the light sources and detectors, wherein the processor calculates a transform of time variations of at least a portion of the spatial images to distinguish between target and non-target image information based on differing frequency behaviors.

5. The apparatus of claim 4, wherein the transform of the time variations of at least a portion of the spatial image information is a discrete Fourier transform.

6. The apparatus of claim 4, wherein the processor further calculates a transform of at least a portion of the spatial image information to further distinguish between target and non-target image information based on differing inverse spatial behaviors.

7. The apparatus of claim 4, wherein the processor further calculates a change in tissue health selected from decubitus ulcers, cancerous lesions, skin transfers, skin temperature, skin oxygenation, burns, skin trauma, skin diseases, autoinflammatory diseases, autoimmune diseases, infectious diseases, and combinations thereof from one or more images captured by the one or more detectors.

8. The apparatus of claim 4, wherein the transform of at least a portion of the spatial image information is a Hough transform.

9. The apparatus of claim 4 further comprising an absorbing enclosure having raised sides to allow light reflected from the target to reach the one or more detectors to reduce or eliminate specular and near surface reflections incident on the detectors.

10. The apparatus of claim 4, further comprising one or more distance standards positioned at a known distance from the detector.

11. The apparatus of claim 4, further comprising one or more intensity reference standards positioned to diffusely reflect light from the light sources into the detector to calibrate the detector.

12. The apparatus of claim 4, further comprising one or more object references positioned to diffusely reflect light from the light sources into the detector to calibrate the detector.

13. The apparatus of claim 4, wherein the two or more light sources comprise light emitting diodes under control of the processor, wherein the processor can individually trigger each of the light emitting diodes or combinations thereof.

14. The apparatus of claim 4, wherein the light sources, and the detector are parallel to the target surface.

15. The apparatus of claim 4, wherein the processor further detects the interface between target and non-target portions of an image captured by the detector.

16. The apparatus of claim 4, wherein one or more detectors are positioned in a pressurizable chamber to illuminate the target surface.

17. The apparatus of claim 16, wherein the pressure within the chamber is controlled by the processor.

18. The apparatus of claim 4, wherein the processor can determine when a property of the target is at a preset level.

19. The apparatus of claim 4, wherein the processor can trigger an alarm if the processor detects one or more of the following parameters: a change in surface conditions, movement, moisture, temperature changes, a solid object, a liquid, a vital sign, oxygenation changes, pressure, pulse rate, and respiration rate.

20. The apparatus of claim 4, wherein the processor takes any of continuous and semi-continuous measurements.

21. The apparatus of claim 4, wherein the processor uses time based information and trends to perform various functions, comprising any of: estimation of precision, estimation of confidence intervals, and prediction of future events.

22. The apparatus of claim 4, further comprising one or more sources of background light.

23. The apparatus of claim 4, further comprising a patient support capable of moving the target in two or three dimensions.

24. The apparatus of claim 4, further comprising a patient support capable of moving the target in two or three dimensions, and the support comprises a pressurized chamber.

25. The apparatus of claim 4, further comprising a patient support and apparatus capable of capturing an entire patient image in one or more target images.

26. The apparatus of claim 4, wherein the two or more light sources and detectors comprise part of an array of imaging cells capable of concurrently capturing an entire patient image.

27. The apparatus of claim 4, wherein the one or more light sources and the one or more detectors are within a mattress.

28. The apparatus of claim 4, wherein the apparatus is handheld.

29. The apparatus of claim 4, wherein the processor turns off one or more light sources within an array of light sources that cause specular reflections of the target support incident on the detectors.

30. An apparatus for noninvasive measurement of a target versus a non-target, comprising:
   one or more imaging cells wherein each imaging cell comprises:
   an imaging chip that comprises a lens;
   one or more light sources located adjacent to the imaging chip, wherein the one or more light sources have a defined emission spectra and angle of illumination and illuminate a portion of the target not including a given image point on the target wherein the one or more light sources are configured to not contact the target;

wherein the imaging chip is positioned to capture a target reflection comprising one or more two dimensional spatial images of the target without contacting the target; and a processor in communication with the imaging cells, wherein the processor calculates a transform of at least a portion of the one or more spatial images to distinguish between a target portion and a non-target portion in the two dimensional spatial images based on differing inverse spatial behaviors between the target and the non-target.

31. The apparatus of claim 30, wherein the processor further calculates a transform of one or more time variations of the at least a portion of the spatial images to further distinguish between target and non-target based on differing frequency behaviors.

32. The apparatus of claim 30, wherein the transform of the at least a portion of the spatial image information is a discrete Fourier transform.

33. The apparatus of claim 30, wherein the transform of the at least a portion of the spatial image information is a Hough transform.

34. An apparatus for detecting conditions of a portion of a living body target versus a non-target that lead to a change in tissue health, comprising:

one or more imaging cells wherein each imaging cell comprises:

an imaging chip that comprises a lens;

one or more light sources located adjacent to the imaging chip, wherein the one or more light sources have a defined emission spectra and angle of illumination and illuminate a portion of the living body not including a given image point on the body wherein the one or more light sources are configured to not contact the target;

wherein the imaging chip is positioned to capture a reflection from the living body comprising one or more two dimensional spatial images of the target without contacting the body; and a processor in communication with the imaging cells, wherein the processor calculates a transform of time variations of the at least a portion of the spatial images to distinguish between target and non-target image information based on differing frequency behaviors to determine the presence of one or more factors that lead to a change in tissue health.

35. The apparatus of claim 34, wherein the changes in tissue health selected from decubitus ulcers, cancerous lesions, skin transfers, skin temperature, skin oxygenation, burns, skin trauma, skin diseases, autoinflammatory diseases, autoimmune diseases, infectious diseases, and combinations thereof.

36. A method for noninvasive measurement of a target versus a non-target, comprising:

illuminating a portion of a target not including a given image point on the target with two or more light sources each of the light sources having a defined emission spectra and angle wherein the two or more light sources do not contact the target;

capturing one or more images with one or more detectors positioned to capture a target reflection without contacting the target, the images comprising one or more two dimensional spatial images of the target; and calculating a transform of time variations of the at least a portion of the spatial images to identify frequency behaviors associated with the target to distinguish between target and non-target image information based on differing frequency behaviors.

37. The method of claim 36, wherein the transform of the time variations of at least a portion of the spatial image information is a discrete Fourier transform.

38. The method of claim 36, wherein a processor further calculates a transform of at least a portion of the spatial image information to further distinguish between target and non-target image information based on differing inverse spatial behaviors.

39. The method of claim 36, wherein the transform of at least a portion of the spatial image information is a Hough transform.

40. The method of claim 36, further comprising the step of:

housing an imaging cell in an absorbing enclosure having raised sides to cause light from the two or more light sources to be reflected from the target to reach the one or more detectors to reduce or eliminate specular reflectance incident on the detectors.

41. The method of claim 36, wherein a target has changes in tissue health selected from one or more decubitus ulcers, cancerous lesions, skin transfers, skin temperature, skin oxygenation, burns, skin trauma, skin diseases, autoinflammatory diseases, autoimmune diseases, infectious diseases, and combinations thereof.

42. The method of claim 36, wherein the two or more light sources comprise light emitting diodes under control of a processor, wherein the processor can individually trigger each of the light emitting diodes.

43. The method of claim 36, wherein the two or more light sources and the one or more detectors are positioned in a pressurizable chamber to illuminate the target surface.

44. The method of claim 36, wherein a processor can detect a non-target including: a mattress, a mattress cover, a sheet, a jewelry, a bandage, an outline of a patient or a fluid.

45. The method of claim 36, wherein a processor takes any of continuous and semi-continuous measurements.

46. The method of claim 36, wherein a processor uses time based information and trends to perform various functions, comprising any of: estimation of precision, estimation of confidence intervals, and prediction of future events.

47. A method for noninvasive measurement of a target versus a non-target, comprising:

illuminating a portion of a target not including a given image point on the target with two or more light sources each of the light sources having a defined emission spectra and angle wherein the two or more light sources do not contact the target;

capturing one or more images with one or more detectors positioned to capture a target reflection without contacting the target, the images comprising one or more two dimensional spatial images of the target; and calculating a transform of at least a portion of the one or more spatial images to identify frequency behaviors associated with the target to distinguish between a target portion and a non-target portion in the two dimensional spatial images based on differing inverse spatial behaviors between the target and the non-target.

48. The method of claim 47, wherein a target is a decubitus ulcer or precursor thereof.

49. An apparatus for noninvasive measurement of physiological conditions of a tissue, comprising:

a base comprising two or more arrays, each array comprising two or more imaging cells wherein each imaging cell comprises an imaging chip that comprises a lens and each imaging cell comprises two or more light sources located adjacent to the imaging chip with each of the light sources having a defined emission spectra and angle of illumination wherein the two or more light sources are configured to not contact the tissue and each of the light sources illuminates a portion of the tissue not including a given image point on the tissue, and wherein the imaging chip is positioned to receive light reflected from the tissue without contacting the tissue;

a processor in communication with the imaging cells, wherein the processor calculates a transform of at least a portion of the one or more spatial images to distinguish between a target portion and a non-target portion in the two dimensional spatial images based on differing inverse spatial behaviors between a target and a non-target; and an input/output module connected to the processor that provides optical and/or electrical signals between the base module and a source of electrical power for the processor, the light sources and the imaging chips.

50. An apparatus for noninvasive measurement of physiological conditions on the surface of the skin, comprising:

a base comprising two or more arrays, each array comprising two or more imaging cells wherein each imaging cell comprises an imaging chip that comprises a lens and each imaging cell comprises two or more light sources located adjacent to the imaging chip with each of the light sources having a defined emission spectra and angle of illumination wherein the two or more light sources are configured to not contact the skin, and wherein the imaging chip is positioned to receive light reflected from the skin without contacting the skin, wherein the light source emission angles are selected to optimize the amount of light that is transmitted through an interface between the light array and the skin, while minimizing the light that is reflected off of the surface that would be directly incident on the imaging chip by illuminating a portion of the skin not including a given image point on the skin;

a processor in communication with the imaging cells wherein the processor calculates a transform of time variations of the at least a portion of the spatial images to distinguish between target and non-target image information based on differing frequency behaviors; and an input/output module connected to the processor that provides optical and/or electrical signals between the base module and a source of electrical power for the processor, the light sources and the imaging chips.

51. A system for noninvasive measurement of physiological conditions on the surface of the skin, wherein the target is a human patient comprising:

a base comprising two or more arrays, each array comprising two or more imaging cells wherein each imaging cell comprises an imaging chip that comprises a lens and each imaging cell comprises two or more light sources located adjacent to the imaging chip with each of the light sources having a defined emission spectra and angle of illumination wherein the two or more light sources are configured to not contact the skin, and wherein the imaging chip is positioned to receive light reflected from the skin without contacting the skin, wherein the light source emission spectra and angle of illumination are selected to optimize the amount of light that is transmitted through an interface between the light array and the skin, while minimizing the light that is reflected off of the surface that would be directly incident on the imaging chip by illuminating a portion of the skin not including a given image point on the skin; and a processor in communication with the imaging cells, wherein the processor calculates a transform of time variations of the at least a portion of the spatial images to distinguish between target and non-target image information based on differing frequency behaviors;

wherein the processor can trigger an alarm if the processor detects a change in a parameter of a non-target, the presence of a non-target, absence of a previously present non-target, or movement of a target or non-target, including: a change in surface conditions, movement, moisture, temperature changes, a solid object, a liquid, and oxygenation changes and the processor can detect a non-target including: a mattress, a mattress cover, a sheet, a wedding ring, an outline of a patient or a fluid.

52. A system for noninvasive evaluation of a target versus a non-target on a living target, comprising:

one or more imaging cells wherein each imaging cell comprises:

an imaging chip that comprises a lens;

two or more light sources located adjacent to the imaging chip, wherein the two or more light sources are directed at the target and illuminate a portion of the target not including a given image point on the target wherein the two or more light sources are configured to not contact the target;

wherein the imaging chip is positioned to capture light reflected from the target comprising one or more two dimensional spatial images of the target without contacting the target; and a processor in communication with the imaging cells, wherein the processor calculates a transform of time variations of the at least a portion of the spatial images to distinguish between target and non-target image information based on differing frequency behaviors, wherein the living background values in the spatial images of the target are separated from non-target values; and a display that shows an image that shows where non-targets are located at or about the surface of the human body or in between the human body and an item of clothing.

53. The system of claim 52, wherein the processor can trigger an alarm if the processor detects a change in a parameter of a non-target, the presence of a non-target, absence of a previously present non-target, or movement of a target or non-target.

54. The system of claim 52, wherein the processor can detect a non-target including: a weapon, a metal, a plastic, a cloth or a container.

* * * * *